United States Patent [19]

Pearlman

[11] Patent Number: 4,549,030
[45] Date of Patent: Oct. 22, 1985

[54] ORGANIC COMPOUNDS AND PROCESS

[75] Inventor: Bruce A. Pearlman, Kalamazoo, Mich.

[73] Assignee: The Upjohn Company, Kalamazoo, Mich.

[21] Appl. No.: 547,317

[22] Filed: Oct. 31, 1983

Related U.S. Application Data

[63] Continuation-in-part of Ser. No. 449,115, Dec. 13, 1982.

[51] Int. Cl.$^4$ ............................................ C07D 317/44
[52] U.S. Cl. .................................. 549/435; 560/121
[58] Field of Search ........................................ 549/435

[56] References Cited

U.S. PATENT DOCUMENTS

| | | | |
|---|---|---|---|
| 3,821,255 | 6/1974 | Kelly | 549/305 |
| 3,953,470 | 4/1976 | Crabbe et al. | 549/435 |
| 4,011,335 | 3/1977 | Hangartner et al. | 549/435 |
| 4,060,534 | 11/1977 | Bundy | 560/121 |
| 4,088,775 | 5/1978 | Skuballa et al. | 549/435 |

FOREIGN PATENT DOCUMENTS 0113561 7/1984 European Pat. Off. ............ 549/435

OTHER PUBLICATIONS

Ochiai et al., Tetrahedron Letters 23 (21), pp. 2205–2208, (1982).
Corey et al., Journ. Amer. Chem. Soc. 92(2), pp. 397–398, (1970).
Corey et al., Journ. Amer. Chem. Soc. 91(20), p. 5675, (1969).

Primary Examiner—Ethel G. Love
Attorney, Agent, or Firm—Lawrence T. Welch

[57] ABSTRACT

The present invention provides a novel process for preparing known prostaglandins, particularly 9-deoxo-9-methylene-16,16-dimethyl-PGE$_2$. This well known and useful prostaglandin is prepared from D-glucose through a series of efficient reactions. Also provided are novel intermediates which are useful for preparation of a wide variety of prostaglandins.

1 Claim, No Drawings

ORGANIC COMPOUNDS AND PROCESS

CROSS REFERENCE TO RELATED APPLICATIONS

This application is a continuation-in-part of copending application Ser. No. 449,115, filed Dec. 13, 1982.

BACKGROUND

The present invention provides a novel process for preparing known compounds. This invention also provides novel intermediates to be used in this process. More particularly, the present invention provides a novel process for preparing prostaglandins from D-glucose, and novel intermediates to be used therein.

The prostaglandins are a family of compounds which are derivatives of prostanoic acid. (See, e.g., Bergstrom, et al., Pharmacol. Rev. 20:1 (1968), and references cited therein.) A trivial system of nomenclature has been divised for this class of compounds, see, N. A. Nelson, Journal of Medicinal Chemistry, 17:911 (1974). This system of nomenclature is used below.

The prostaglandins are known to be useful for a wide variety of pharmaceutical purposes including decreasing blood pressure, stimulating smooth muscles, inhibiting gastric secretion, controlling spasms and facilitating breathing in asthmatic conditions, decongesting nasal passages, decreasing blood platelet adhesion and inhibiting blood platelet aggregation and thrombis formation, and a variety of uses in the reproductive area including labor induction, abortion, cervical dilatation, estrus regulation, and menstrual regulation. For a recent discussion of prostaglandins which are currently being developed commercially, see N. A. Nelson, et al., Chemical and Engineering News, pp. 30–44 (Aug. 16, 1982).

9-Deoxy-9-methylene-PGE-type compounds are disclosed in U.S. Pat. No. 4,060,534. 9-Deoxo-9-methylene-16,16-dimethyl-prostaglandin E2 (formula I), has been given the generic name meteneprost. This prostaglandin is useful in the reproductive area; more particularly, it is useful for menses induction and cervical dilatation. The prior art process set forth in the '534 patent cited above produces meteneprost from the cyclopentane-lactone compound of the formula II using a 14 step sequence. This cyclopentane-lactone compound is itself prepared by a 9 step sequence from norbornadiene. The final product produced by this process is contaminated by varying amounts of the corresponding 5,6-trans isomer, the separation of which requires an exceedingly difficult and laborous chromaographic process. Thus, this process is not satisfactory for large scale commercial production of this material.

PRIOR ART

Meteneprost and its method of synthesis are described in U.S. Pat. No. 4,060,534. Two routes for the total synthesis of prostaglandins are described in Kelly, U.S. Pat. No. 3,821,255 and divisions thereof; and two articles by Corey, et al.: J. Am. Chem. Soc. 91:5675 (1969), and J. Am. Chem. Soc. 921, 397 (1970). A methylenation process is disclosed in Fujita, et al., Tet. Lett. 23:2205 (1982).

SUMMARY OF THE INVENTION

The present invention provides:
(1) a compound of the formula A-6A, wherein $R_1$ is
  (a) $-CO_2M$, wherein M is a metal cation,
  (b) $-CN$,
  (c) $-CO_2R_{21}$,
  (d) $-CONHR_2$,
  (e) $-CON(R_2)_2$, wherein each $R_2$ is the same or different,
  (f) $-CH=NR_3$,
  (g) $-CHNOR_3$, or
  (h) $-CHNN(R_3)_2$;
  wherein $R_2$ is
  (a) $(C_1-C_5)$alkyl, or
  (b) $(C_6-C_{12})$aryl;
  wherein $R_3$ is
  (a) hydrogen,
  (b) $C_1-C_5$alkyl, or
  (c) $(C_6-C_{12})$aryl;
  wherein $A_1$ is
  (a) cis$-CH_2CH=CH-CH_2-(CH_2)_g-CH_2-$,
  (b) cis$-CH_2CH=CH-CH_2-(CH_2)_g-CF_2-$,
  (c) cis$-CH_2CH_2-CH=CH-(CH_2)_g-CH_2-$,
  (d) $-(CH_2)_4-(CH_2)_g-CH_2-$,
  (e) $-(CH_2)_4-(CH_2)_g-CF_2-$,
  (f) $-CH_2CH_2-O-CH_2-(CH_2)_g-CH_2-$,
  (g) $-CH_2C\equiv C-CH_2-(CH_2)_g-CH_2-$, or
  (h) $-CH_2CH_2-C\equiv C-(CH_2)_g-CH_2-$, and
  wherein g is one 2 or 3;
  wherein $R_4$ is
  (a) hydrogen,
  (b) $-OR_2$,
  (c) $-OSO_2R_2$,
  (d) $-OSi(R_2)_3$, wherein each $R_2$ is the same or different,
  (e) $-CH(OR_2)_2$, wherein each $R_2$ is the same or different, or
  (f) $-CN$; and
  wherein $R_{21}$ is $(C_2-C_8)$alkyl;

(2) a process for preparing a prostaglandin intermediate of the formula A-6 which comprises:
  (a) treating a compound of the formula A-5 with a weakly nucleophilic strong base in an inert solvent at a temperature in the range of about $-110°$ to about $-30°$ C.; and, subsequently
  (b) adding an alkylating agent of the formula B-4 at a temperature in the range of about $-110°$ to about $-30°$ C.;

(3) a process for preparing 9-deoxo-9-methylene-16,16-dimethyl-PGE$_2$ of the formula I which comprises:
  (a) treating an alkyl ester of the formula A-6 with aqueous sulfuric acid, followed by sodium periodate and then by sodium borohydride to convert the 5,6-acetonide into the corresponding primary hydroxyl;
  (b) chlorinating the hydroxy ester of the formula A-7 thus formed by treatment with a chlorinating agent;
  (c) reducing the chloro-ester of the formula A-8 thus formed by treatment with a hydride donor;
  (d) sulfonating the chloro-alcohol of the formula A-9 thus formed by treatment with iodine, triphenylphosphine, and imidazole, followed by benzyltrimethylammonium p-toluene-sulfinate;
  (e) cyclizing the chlorosulfone of the formula A-10 thus formed by reacting it with potassium tert-butoxide;
  (f) methylenating the cyclized sulfone of the formula A-11 thus formed;
  (g) connecting the beta chain to the 9-methylene cyclopentane of the formula A-12 thus formed by treatment with periodic acid, followed by treatment with a salt of a phosphonate of the formula $(CH_3O)_2-P(O)-CH_2-C(O)-C(CH_3)_2-(CH_2)_3-CH_3$;

(h) reducing the chloro-enone prostaglandin of the formula A-13 thus formed by treatment with DIBAL/BHT reagent; and (i) replacing the chloride of the chloroenone-prostaglandin of the formula A-14 thus formed with a carboxylic acid by successive treatments with potassium cyanide and potassium hydroxide to yield 9-deoxo-9-methylene-16,16-dimethyl-PGE$_2$;

(4) a process for preparing a compound of the formula A-5 which comprises:

(a) isopropylidenating D-glucose of the formula A-1 by treating it with anhydrous zinc chloride in the presence of phosphoric acid;

(b) oxidizing the diacetone-glucose of the formula A-2 thus formed by treatment with pyridinium chlorochromate and 3 Angstrom molecular sieves;

(c) condensing the diacetone-glucose-ketone of the formula A-3 thus formed with a compound of the formula C-5 in the presence of potassium tert-butoxide at a temperature of from about $-30°$ to about $0°$ C.; and (d) hydrogenating the ester of the formula A-4 thus formed to yield the formula A-5 compound;

(5) a compound of the formula A-5A wherein $R_1$ is
 (a) $-CO_2M$, wherein M is a metal cation,
 (b) $-CN$,
 (c) $-CO_2R_{21}$,
 (d) $-CONHR_2$,
 (e) $-CON(R_2)_2$, wherein each $R_2$ is the same or different;
 (f) $-CH=NR_3$,
 (g) $-CHNOR_3$, or
 (h) $-CHNN(R_3)_2$
wherein $R_2$ is
 (a) $(C_24 C_5)$alkyl, or
 (b) $(C_6-C_{12})$aryl;
wherein $R_3$ is
 (a) hydrogen,
 (b) $(C_1-C_5)$alkyl, or
 (c) $(C_6-C_{12})$aryl; and
wherein $R_{21}$ is $(C_2-C_5)$alkyl; and (6) a compound of the formula A-7A wherein $R_1$ is
 (a) $-CO_2M$, wherein M is a metal cation,
 (b) $-CN$,
 (c) $-CO_2R_2$,
 (d) $-CONHR_2$,
 (e) $-CON(R_2)_2$, wherein each $R_2$ is the same or different;
 (f) $-CHNR_2$,
 (g) $-CHNOR_3$, or
 (h) $-CHNN(R_3)_2$;
wherein $R_2$ is
 (a) $(C_1-C_5)$alkyl, or
 (b) $(C_6-C_{12})$aryl;
wherein $R_3$ is
 (a) hydrogen,
 (b) $(C_1-C_5)$alkyl, or
 (c) $(C_6-C_{12})$aryl;
wherein $A_1$ is
 (a) cis—$CH_2CH=CH-CH_2-(CH_2)_g-CH_2-$,
 (b) cis—$CH_2CH=CH-CH_2-(CH_2)_g-CF_2-$,
 (c) cis—$CH_2CH_2-CH=CH-(CH_2)_g-C_2-$,
 (d) $-(CH_2)_4-(CH_2)_g-CH_2-$,
 (e) $-(CH_2)_4-(CH_2)_g-CF_2-$,
 (f) $-CH_2CH_2-O-CH_2-(CH_2)_g-CH_2-$,
 (g) $-CH_2C\equiv C-CH_2-(CH_2)_g-CH_2-$, or
 (h) $-CH_2CH_2-C\equiv C-(CH_2)_g-CH_2-$,
wherein g is one, 2 or 3;
wherein $R_4$ is
 (a) hydrogen,
 (b) $-OR_2$,
 (c) $-OSO_2R_2$,
 (d) $-OSi(R_2)_3$, wherein each $R_2$ is the same or different,
 (e) $-CH(OR_2)_2$, wherein each $R_2$ is the same or different,
 (f) $-CN$, or
 (g) $-OC(R_2)_3$;
wherein $R_5$ is
 (a) $-OH$,
 (b) $-OR_{18}$,
 (c) halogen, or
 (d) $-OSO_2R_2$; and
wherein $R_{18}$ is a hydroxy protecting group or a silyl protecting group;

(7) a process for preparing a compound of the formula A-12 which comprises:

(a) treating a chloro-alcohol of the formula A-9 with triphenylphosphine, imidazole, and iodine, followed by sodium cyanide;

(b) treating the uncyclized nitrile of the formula C-1 thus formed with a weakly nucleophilic strong base in an inert solvent; and (c) reacting the cyclized nitrile of the formula C-2 thus formed successively with lithium diisopropylamide, iodomethyltributyltin, and methyl lithium to yield the formula A-12 compound;

(8) a compound of the formula A-11A, wherein $A_1$ is
 (a) cis—$CH_2CH=CH-CH_2-(CH_2)_g-CH_2-$,
 (b) cis—$CH_2CH=CH-CH_2-(CH_2)_g-CF_2-$,
 (c) cis—$CH_2CH_2-CH=CH-(CH_2)_g-CH_2-$,
 (d) $-(CH_2)_4-(CH_2)_g-CH_2-$,
 (e) $-(CH_2)_4-(CH_2)_g-CF_2-$,
 (f) $-CH_2CH_2-O-CH_2-(CH_2)_g-CH_2-$,
 (g) $-CH_2C\equiv C-CH_2-(CH_2)_g-CH_2-$, or
 (h) $-CH_2CH_2-C\equiv C-(CH_2)_g-CH_2-$,
wherein $R_2$ is
 (a) $(C_1-C_5)$alkyl, or
 (b) $(C_6-C_{12})$aryl;
wherein $R_3$ is
 (a) hydrogen,
 (b) $(C_1-C_5)$alkyl, or
 (c) $(C_6-C_{12})$aryl;
wherein $R_4$ is
 (a) hydrogen,
 (b) halogen,
 (c) $-OR_2$,
 (d) $-OSO_2R_2$,
 (e) $-OSi(R_2)_3$, wherein each $R_2$ is the same or different,
 (f) $-CH(OR_2)_2$, wherein each $R_2$ is the same or different, or
 (g) $-CN$, and
wherein W is divalent and is
 (a) $-H$, $-SO_2(C_6H_5)$,
 (b) $-H$, $-CN$,
 (c) $=P(C_6H_5)_3$,
 (d) $-H$, $-PO(C_6H_5)_2$,
 (e) $CH_3CH(OCH_2CH_3)O-$, $-CN$.
 (f) $-H$, $-SO_2CH_3$,
 (g) $CH_3S-$, $CH_3S-$, (h) —H, —NO$_2$, or
(i) —H, —SO(CH$_6$H$_5$);

(9) a process for preparing PGF$_2\alpha$ which comprises
  (a) treating the cyclized sulfone of formula A-11 with lithium diisopropyl amide in THF followed by acetone and then sodium amalgam;
  (b) connecting the beta chain to the tetrasubstituted olefin of formula D-2 thus formed by successive treatments with periodic acid and the potassium salt of dimethyl 2-oxo-heptylphosphonate;
  (c) selectively cleaving the tetrasubstituted double bond of the tri-olefin of formula D-3 thus formed by treatment with sodium periodate in the presence of a catalytic amount of osmium tetroxide;
  (d) stereospecifically reducing the diketone of formula D-4 thus formed by treatment with DIBAL/BHT reagent; and
  (e) replacing the chlorine atom of the prostaglandin of formula D-5 thus formed with a carboxylic acid group by successive treatments with potassium cyanide and potassium hydroxide to yield PGF$_2\alpha$;

(10) a process for preparing PGF$_2\alpha$ which comprises:
  (a) treating a compound of the formula A-11A, wherein W is CH$_3$OH(OCH$_2$CH$_3$)O$_1$CN; A$_1$ is cis—CH$_2$CHCH(CH$_2$)$_3$; R$_2$ and R$_3$ are CH$_3$; and R$_4$ is Cl, with periodic acid followed by dimethyl-2-oxo-heptylphosphonate;
  (b) reducing the carbonyl group of the compound of formula E$_1$ thus formed by treatment with DIBAL/BHT reagent;
  (c) replacing the protected cyanohydrin group of the compound of the formula E$_2$ thus formed with a hydroxyl group with the $\alpha$ orientation by successive treatments with aqueous sulfuric acid and lithium tri-sec-butylborohydride; and
  (d) replacing the chlorine atom of the prostaglandin of formula D-5 thus formed with a carboxylic acid group by successive treatments with potassium cyanide and potassium hydroxide to yield PGF$_2\alpha$;

(11) a process for preparing PGF$_2\alpha$ which comprises:
  (a) treating the compound of the formula A-11A (wherein W is CH$_3$S, CH$_3$S; A$_1$ is cis CH$_2$CHCH(CH$_2$)$_3$; R$_2$ and R$_3$ are CH$_3$; and R$_4$ is Cl) with aqueous sulfuric acid followed by sodium borohydride;
  (b) converting the thioketal group of the tri-hydroxy compound of formula E-1 thus formed into a hydroxyl group with the $\alpha$ orientation by successive treatments with mercuric ion and DIBAL/BHT reagent;
  (c) connecting the beta chain to the tetra-hydroxy compound of formula F-2 thus formed by successive treatments with sodium periodate, and dimethyl-2-oxo-heptylphosphonate;
  (d) reducing the carbonyl group of the dihydroxy compound of formula F-3 thus formed by treatment with DIBAL/BHT reagent; and
  (e) replacing the chlorine atom of the prostaglandin of the formula D-5 thus formed with a carboxylic acid group by successive treatments with potassium cyanide and potassium hydroxide to yield PGF$_2\alpha$;

(12) a process for preparing PGE$_2$ which comprises:
  (a) treating the compound of the formula A-11A (wherein W is H, NO$_2$; A$_1$ is cis CH$_2$CHCH(CH$_2$)$_3$; R$_2$ and R$_3$ are CH$_3$; R$_4$ is Cl) with periodic acid followed by dimethyl-2-oxo-heptylphosphonate;
  (b) reducing the carbonyl group of the enone compound of the formula G-2 thus formed by treatment with DIBAL/BHT reagent;
  (c) replacing the chlorine atom of the nitro-dihydroxy compound of the formula G-3 thus formed with a carboxylic acid group by successive treatments with potassium cyanide and potassium hydroxide;
  (d) replacing the nitro group of the dihydroxy compound of the formula G-4 thus formed with a carbonyl group by treatment with titanium trichloride to yield PGE$_2$; and

(13) a process for preparing a compound of the formula A-12 which comprises:
  (a) treating the chloro-alcohol of the formula A-9 with triphenylphosphine, imidazole, and iodine in toluene followed by sodium methyl mercaptide in methanol followed by meta-chloroperbenzoic acid in methylene chloride;
  (b) treating the chloro-sulfone of the formula A-10A (wherein W is H, SO$_2$CH$_3$, R$_4$ and R$_5$ are Cl; R$_2$ amd R$_3$ are CH$_3$; and A$_1$ is cis CH$_2$CHCH(CH$_2$)$_3$) thus formed with potassium tert-butoxide and iodine in THF to yield the formula A-12 compound.

The carbon atom content of various hydrocarbon-containing moieties is indicated by a prefix designation the minimum and maximum number of carbon atoms in the moiety, i.e., the prefix (C$_i$-C$_j$) indicates a moiety of the integer "i" to the integer "j" carbon atoms, inclusive. Thus, (C$_1$-C$_3$)alkyl refers to alkyl of one to 3 carbon atoms, inclusive, or methyl, ethyl, propyl, and isopropyl.

Examples of halogen include chloro, fluoro, bromo, or iodo. Examples of metal cations include sodium, potassium, and lithium.

W is a divalent moiety. Thus, when W is defined as e.g., "—H, —CN," this means that W designates an $\alpha$-hydrogen, $\beta$-cyano or $\beta$-hydrogen, $\alpha$-cyano moiety.

Examples of weakly nucleophilic strong bases employed in step 5 of the process of this invention include alkali metal amide bases such as lithium hexamethyldisilazide, lithium amide, lithium di-isopropyl amide, lithium isopropylcyclohexyl amide, lithium dicyclohexylamide, sodium hexamethyldisilazide, potassium hexamethyl disilazide, and the like. Use of sodium and potassium bases result in a higher ratio of the desired product (A-6) to the undesired C-8 epimer (Table I).

TABLE I

| Base | Temp. | C-8 Isomer Ratio ($^{c-6}$/epi) |
| --- | --- | --- |
| LiN(SiMe$_3$)$_2$ | $-20°$ | 92/8 |
| LiN(SiMe$_3$)$_2$ | $-70°$ | 96/4 |
| NaN(SiMe$_3$)$_2$ | $-20°$ | 97/3 |
| NaN(SiMe$_3$)$_2$ | $-70°$ | 99/1 |
| KN(SiMe$_3$)$_2$ | $-20°$ | 97/3 |
| KN(SiMe$_3$)$_2$ | $-70°$ | 99/1 |

Use of low temperature ($-70°$) also favors a high isomer ratio. However, formation of a small amount of the undesired C-8 epimer is of little practical consequence, since the C-8 epimeric material can be separated either by stopping the step 10 reaction at approximately 92% conversion of by crystallization of the step 10 product.

Suitable chlorinating agents employed in step 7 include mesylchloride and lithium chloride in DMF, phorphorus oxychloride in DMF, oxalylchloride in DMF, sulfuryl chloride in pyridine, phosphorus pentachloride in DMF, thionyl chloride in pyridine, phosgene in DMF, and the like. Mesyl chloride and lithium chloride in DMF is the most preferred chlorinating agent for use in this step.

Suitable hydride donors employed in step 9 include lithium aluminum hydride, lithium borohydride, diisobutylaluminum hydride, sodium bis(2-methoxyethoxy)aluminum hydride, and the like. Lithium aluminum hydride is the most preferred hydride donor.

Suitable solvents for the alkylation step include: tetrahydrofuran (THF); dimethoxyethane; ether; ammonia; t-butylmethylether; toluene; dimethylformamide (DMF); acetonitrile; and dimethylsulfoxide (DMSO). THF is the most preferred solvent. While temperatures in the range of $-110°$ to $-30°$ C. are employed in step 6, it is preferable to use temperatures of from $-78°$ to $-30°$ C.

Suitable salts of the beta chain phosphonate (step 12) are any of those suitable in Wittig reactions. These are well known to those skilled in the art. See, e.g., U.S. Pat. No. 4,060,534 and references cited therein. Thus, alkalai metal salts, such as sodium, potassium, and lithium are employed. The sodium salt is preferred in this step.

The silyl protecting groups within the scope of $R_{18}$ are of the formula $-Si(G_1)_3$. $G_1$ is alkyl of one to 4 carbon atoms, cycloalkyl of 3 to 10 carbon atoms, inclusive, aralkyl of 7 to 12 carbon atoms, inclusive, phenyl, or phenyl substituted with one or 2 fluoro, chloro, or alkyl of one to 4 carbon atoms, with the proviso that in a $-Si(G_1)_3$ moiety the various $G_1$'s are the same or different and at least one $G_1$ is hindered (such as tert-butyl). Silyl groups within the scope of $-Si(G_1)_3$ include triethylsilyl, triisopropyl silyl, triphenylsilyl, t-butyldimethylsilyl, methylphenylbenzylsilyl, and tert-butyl-diphenyl silyl. With regard to $G_1$, examples of alkyl are methyl, ethyl, isopropyl, propyl, isobutyl, butyl, sec-butyl, tert-butyl, pentyl, and the like. Examples of aralkyl are benzyl, phenethyl, α-phenylethyl, 3-phenylpropyl, α-maphthylmethyl, and 2-(α-maphthyl)ethyl. Examples of phenyl substituted with halo or alkyl are p-chlorophenyl, m-fluorophenyl, o-tolyl, 2,4-dichlorophenyl, p-tert-butylphenyl, 4-chloro-2-methylphenyl, and 2,4-dichloro-3-methylphenyl. $G_1$ may also be a phenoxy group, for example of a silyl protecting group containing a phenoxy group that has been disclosed in the literature is 2,4,6-tri-tert-butyl-phenoxy dimethylsilyl. Tert-butyldimethylsilyl is most preferred as a silylating agent.

These silyl groups are known in the art. See for example, Pierce "Silylating of Organic Compounds," Pierce Chemical Company, Rockford Ill. (1968). When silylated products of the charts below are intended to be subjected to chromatographic purification, then the use of silyl groups known to be unstable to chromatography is to be avoided. Further, when silyl groups are to be introduced selectively, silylating agents which are readily available and known to be useful in selective silylations are employed. For example, t-butyldiphenylsilyl and t-butyldimethylsilyl groups are employed when selective introduction is required. A particularly useful silyl group for this purpose is t-butyldimethylsilyl, although other silyl groups are likewise employed.

The hydroxy protecting groups within the scope of $R_{18}$ are any group which replaces a hydroxy hydrogen and is neither attacked by nor is as reactive to the reagents used in the transformations used herein as a hydroxy is and which is subsequently replaceable by acid hydrolysis with hydrogen in the preparation of the prostaglandin-type compounds. Several such protective groups are known in the art, e.g., tetrahydropyranyl, substituted tetrahydropyranyl, t-butoxy-methyl, ethoxy ethyl, methoxy methyl, and 2-methoxy-ethoxy-methyl. See for reference E. J. Corey, Proceedings of the Robert A. Welch Foundation Conferences on Chemical Research, XII Organic Synthesis, pgs. 51–79 (1969). Those blocking groups which have been found useful include:

(a) tetrahydropyranyl;
(b) tetrahydrofuranyl;
(c) acid-labile ethers such as tert-butyl or triphenylmethyl; and
(d) a group of the formula $-C(OR_{11})(R_{12})-CH(R_{13})(R_{14})$, wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are hydrogen or alkyl of one to 4 carbon atoms, inclusive, phenyl, phenyl substituted with one, 2, or 3 alkyl of one to 4 carbon atoms, inclusive, or when $R_{12}$ and $R_{13}$ are taken together $-(CH_2)_a-$ or when $R_{12}$ and $R_{13}$ are taken together $-(CH_2)_b-O-(CH_2)_c$, wherein a is 3, 4, or 5 and b is one, 2 or 3, and c is one, 2, or 3, with the proviso that b plus c is 2, 3, or 4, with the further proviso that $R_{12}$ and $R_{13}$ may be the same or different, and wherein $R_{14}$ is hydrogen or phenyl.

When the blocking group $R_{18}$ is tetrahydropyranyl, the tetrahydropyranyl ether derivative of any hydroxy moieties of the intermediates herein is obtained by reaction of the hydroxy-containing compound with 2,3-dihydropyran in an inert solvent, e.g., dichloromethane, in the presence of an acid condensing agent such as p-toluenesulfonic acid or pyridine hydrochloride. The dihydropyran is used in large stoichiometric excess, preferably 4 to 100 times the stoichiometric amount. The reaction is normally complete in less than an hour at 20°–50° C.

When the protective group is tetrahydrofuranyl, 2,3-dihydrofuran is used, as described in the preceding paragraph, in place of the 2,3-dihydropyran.

When the protective group is of the formula $-C(OR_{11})(R_{12})-CH-(R_{13})(R_{14})$, wherein $R_{11}$, $R_{12}$, $R_{13}$, and $R_{14}$ are as defined above; a vinyl ether or an unsaturated cyclic or heterocyclic compound, e.g., 1-cyclohexen-1-yl methyl ether, or 5,6-dihydro-4-methoxy-2H-pyran is employed. See C. B. Reese, et al., Journal of the Chemical Society 86, 3366 (1967). The reaction conditions for such vinyl ethers and unsaturated compounds are similar to those for dihydropyran above.

The protective groups as defined by $R_{18}$ are removed by mild acidic hydrolysis. For example by reaction with (1) hydrochloric acid in methanol; (2) a mixture of acetic acid, water, and tetrahydrofuran, or (3) aqueous citric acid or aqueous phosphoric acid in tetrahydrofuran, at temperatures below 55° C., hydrolysis of the blocking group is achieved.

Examples of alkyl of one to 5 carbon atoms, inclusive, are methyl, ethyl, propyl, butyl, pentyl and isomeric forms thereof.

Examples of aryl of 6 to 12 carbon atoms, inclusive, are phenyl, benzyl, 2-phenethyl, 1-phenylethyl, 2-phenylpropyl, 4-phenylbutyl, 3-phenylbutyl, 2-(1-naphthylethyl), and 1-(2-naphthylmethyl).

Surprisingly and unexpectedly it has been found that meteneprost and similar prostaglandins may be prepared from D-glucose by the method set forth in Chart A, which is described more fully below. This route is substantially shorter than the prior art process (14 steps for the present process versus 23 for the prior art process). Further, the final product produced is virtually free of all impurities including the 5,6-trans isomer. Therefore, the method of the present invention overcomes many of the problems of the prior art process, and allows for the preparation of large scale commercial quantities of meteneprost and other prostaglandins.

The most significant aspect of this invention is the discovery that the ester of the formula A-5 in Chart A undergoes alkylation with a cis-allylic bromide of the formula A-5A nearly stereospecifically to afford the product of the formula A-6 which possesses all of the asymmetry of the prostaglandin compounds except at the C-15 position. That is, the compound of the formula A-6 has asymmetry at the C-8, C-11, C-12, and the 5,6-cis double bond as does meteneprost. Other commercially useful prostaglandins, such as $PGF_2\alpha$, also have this configuration. Thus, the process and intermediates of the present invention can be used to prepare many other prostaglandins having the same asymmetry as meteneprost at C-8, C-11, and C-12 as well as the 5-6 double bond. This compound of the formula A-6 is thus a very versatile intermediate which can be converted into various prostaglandins by short sequences of efficient reactions. Compounds within the generic formula A-6A are used in the process of this invention to prepare other useful prostaglandins.

All of the compounds encompassed within generic formula A-5A undergo the above-described alkylation reaction to afford the corresponding compounds of generic formula A-6A. However, to obtain maximum advantage from this invention, the substrate compound must be readily produced on a large industrial scale. The compound of formula A-5A wherein $R_1$ is $CO_2CH_3$ and $R_2$ and $R_3$ are methyl, which has been described in the literature (Rosenthal, A.; et al., J. Org. Chem. 34:1029 (1969) and Tet. Lett. 2393 (1967)), is not readily produced because it has a relatively low melting point (57°–58° C.), which makes crystallization out of crude product mixtures difficult.

Surprisingly and unexpectedly, it has been found that the ethyl ester of the formula A-5A wherein $R_1$ is $CO_2CH_2CH_3$, and $R_2$ and $R_3$ are —$CH_3$ possesses a sufficiently high melting point (87°–89° C.) such that it crystallizes readily out of crude product mixtures. Thus, it is preferable to practice the invention using this compound rather than the methyl ester of formula A-5A. The methyl ester is in fact outside the scope of this invention.

The entire synthetic route from D-glucose to meteneprost is set forth in Chart A.

Referring to Chart A, step 1, a suspension of D-glucose (a well-known, readily available compound) in acetone is treated with anhydrous zinc chloride and a catalytic amount of phosphoric acid and then stirred at room temperature. (This reaction is described in U.S. Pat. No. 3,103,508.) After 42 hrs, approximately 46% of the glucose is converted to product. The unreacted glucose is then filtered off and the filtrate is treated with aqueous sodium hydroxide to precipitate the zinc chloride as zinc hydroxide, which is then filtered off. The filtrate is then concentrated until it divides into aqueous and organic phases. The aqueous layer is then extracted with methylene chloride and dried over magnesium sulfate. This solution is used in the next step.

The next step in the synthesis is described in Herscovici, et al. Chem. Soc. Chem. Comm. 561 (1980). A solution of diacetone glucose in methylene chloride from step 1 is treated with pyridinium chlorochromate (PCC) and 3 Angstrom molecular sieves, and then stirred at room temperature until oxidation is complete (approximately 42 hours). The reaction mixture is then filtered to remove the molecular sieves and insoluble chromium salts. To remove the soluble chromium salts, the solution is concentrated down to an oily residue and the product extracted with boiling heptane. The product can be stored at room temperature for at least three weeks (probably indefinitely at 0°).

Step 3 of the synthesis is described in Rosenthal, et al. Tet. Let. 2393 (1967). A solution of Emmons reagent in toluene is treated with potassium tert-butoxide at 0° C. to form the potassium salt. The resulting suspension is then cooled to $-20°$ C. and treated with a solution of diacetone-glucose-ketone in toluene. The reaction is complete in 2.5 hours. The reaction mixture is then worked up simply by washing with dilute aqueous sodium hydroxide, and then concentrating. The crude product (an oil) contains minor impurities by thin-layer chromatography (TLC), but is sufficiently pure for use in the next step.

Step 4 of the synthesis is described in Rosenthal, et al., Tet. Let. 2393 (1967). The crude unsaturated ester is hydrogenated at 50 psi over a 10% palladium-on-carbon catalyst in 95% ethanol. Uptake of hydrogen is rapid even at low catalyst loadings (2%). After filtration of the catalyst, the solvent is evaporated to leave an oil which consists of the indicated ester contaminated with minor impurities. To remove them, this oil is crystallized.

In step 5, a solution of lithium hexamethyldisilazide in tetrahydrofuran (THF) is cooled to $-25°$ C., then treated with a THF solution of the hydrogenated ester. After 5 minutes, a solution of cis-1-bromo-6-chloro-2-hexene (see Chart B for the method of its preparation) is added. Alkylation is probably complete within minutes. However, the temperature is warmed to 0° C. and kept there for 4 hours. The reaction mixture is then worked up to afford an oil containing the indicated alkylated ester and its C8 epimer in a 92:8 ratio (by $^{13}C$-NMR) as well as some unreacted alpha chain bromide and several minor by-products. Separation of the C8 epimeric material can be accomplished either by stopping the step 10 reaction at approximately 92% conversion or by crystallization of the step 10 product so there is no need to chromatograph at this point.

In step 6, a solution of the crude alkylated ester in methanol is treated with aqueous sulfuric acid and stirred at 70° C. until TLC indicates that hydrolysis of the 5,6-acetonide is complete (approximately 5 hours). The reaction mixture is then cooled to 0° C. and treated in succession with aqueous sodium bicarbonate (to adjust the pH to approximately 7), sodium periodate, and sodium borohydride. The reaction mixture is then worked up to afford the indicated hydroxyester as an oil, sufficiently pure for use in the next step.

In step 7, a solution of the hydroxy-ester in DMF is treated with mesyl chloride and lithium chloride in dimethyl formamide (DMF), then stirred at 85° C. for 2 hours. The reaction mixture is then poured into water, extracted with heptane, washed with aqueous sodium bicarbonate, and concentrated to leave an oil which consists of the indicated chloro-ester contaminated with minor amounts of several impurities. This oil is suitable for use in the next step.

In step 8, a solution of the chloro-ester in THF is added to a cooled (0° C.) suspension of lithium aluminum hydride in THF. Approximately 5 minutes after the addition has been completed the excess lithium aluminum hydride is quenched cautiously with aqueous sodium hydroxide. The inorganic salts are then filtered off, and the filtrate is concentrated to an oil which contains the indicated chloro-alcohol together with several minor impurities. This oil is suitable for use in the next step.

In step 9, a solution of the chloro-alcohol in toluene is treated in succession with triphenylphosphine, imidazole, and iodine, and then stirred at room temperature. After 30 minutes, the reaction mixture is washed with aqueous sodium hydroxide, treated with benzyltrimethylammonium p-toluene-sulfinate, stirred at 80° C. for 2.5 hours, washed with aqueous sodium hydroxide, and concentrated to an oil, consisting of a mixture of the indicated sulfone and several minor impurities including the isomeric sulfite ester (a mixture of epimers at sulfur). This oil is then chromatographed.

In step 10, a solution of potassium tert-butoxide in THF is cooled to $-20°$ C. and treated with a solution of the chloro-sulfone in THF. After 30 minutes, conversion to the cyclized sulfone is complete. The reaction mixture is then worked up to afford a yellow oil. This oil is then crystallized from boiling cyclohexane to produce the cyclized sulfone in completely pure form.

In step 11, the cyclized sulfone (Formula A-11) is converted to the 9-methylene cyclopropane (Formula A-12) by any of several methods, utilizing successive treatments of: diisopropylamine, n-butyllithium and iodotributyltin (Example 11); n-butyllithium and dibromomethane (Example 11A); n-butyllithium and diiodomethane (Example 18); n-butyllithium and 2-ethoxymethyl-methyl chloride (Example 19); or lithium, diisopropylamide, iodomethyltributyltin and methyl lithium. Preferably, as in Example 11A, a cooled (approximately $-78°$ C.) solution of the cyclized sulfone in THF is treated with a solution of 3 equivalents of n-butyllithium in hexane followed by 4 equivalents of dibromo-methane. The reaction mixture is worked up to afford a red-brown oil, consisting of the indicated 9-methylene-cyclopentane, in nearly pure form.

The chloro-alcohol of formula A-9 may alternatively be converted into a 9-methylene-cyclopentane (formula A-12) by the steps outlined in Chart C.

In Chart C, the chloro-alcohol of formula A-9 is converted into a chloro-nitrile (formula C-1) by treatment with triphenylphospine, imidazole, and iodine in toluene (room temperature for 50 min) followed by sodium cyanide in dimethyl formamide (DMF) at room temperature for 3.5 hours. The chloronitrile is then converted to the cyclized nitrile (formula C-2) as a 4.3:1.0 mixture of C-9 epimers by treatment with lithium hexamethyldisilazide in toluene at $-20°$ C. for 2 hours. The cyclized nitrile is then converted into the 9-methylene-cyclopentane (formula A-12) by successive treatments with lithium diisopropylamide in THF at $-78°$ C. for 5 minutes, then iodomethyltributyltin at $-78°$ C. for 15 minutes, then excess methyl lithium at $-78°$ C. for 15 minutes.

The chloro-alcohol of the formula A-9 may alternatively be converted into the 9-methylene cyclopentane of the formula A-12 by treatment with triphenylphospine, imidazole, and iodine in toluene (room temperature, 50 minutes) followed by sodium methyl mercaptide in methanol (room temperature, 30 minutes) followed by meta-chloroperbenzoic acid (MCPBA) in methylene chloride ($-20°$ C., 90 minutes) followed by potassium tert-butoxide and iodine in THF (0° C., 1.5 hours).

In step 12, a solution of the 9-methylene-cyclopentane in aqueous THF is treated with periodic acid, then stirred at room temperature until cleavage of the acetonide is complete by TLC (40 minutes). The reaction mixture is then diluted with ethyl acetate and washed with aqueous disodium hydrogen phosphate. The organic phase is then treated with a solution of a salt (preferably the sodium salt) of the beta-chain phosphonate in THF (prepared in advance, e.g., by adding the beta-chain phosphonate to a suspension of sodium hydride in THF). After stirring at room temperature for 2 hours, the reaction mixture is worked up to afford an oil containing the chloroenone together with several minor impurities. The oil is sufficiently pure for use in the next step.

In step 13, reduction of the chloro-enone to chlorometeneprost is undertaken by a process recently disclosed by Iguchi, et al., J. Org. Chem. 44:1363 (1979), which provides for stereoelective reduction of 11-hydroxy-15-keto-prostanoids to 15α-hydroxy-prostanoids. A solution of DIBAL-BHT reagent in toluene is prepared by addition of a solution of diisobutylaluminum hydride (DIBAL) in toluene to a cooled (0° C.) solution of 3,5-di-t-butyl-4-hydroxy-toluene (BHT) in toluene. This solution is then cooled to $-78°$ C. and treated with a solution of the chloro-enone in toluene, and warmed to 0° C. After 1 hour, the reaction mixture is worked up to aford an oil consisting of a 79:21 mixture of chloro-meteneprost and 15-epi-chloro-meteneprost which are separated by chromatography on silica gel.

Finally, in step 14, a solution of chloro-meteneprost in dimethylformamide (DMF) is preferably treated with potassium cyanide, and then heated at 95° C. for 10 hours. The reaction mixture is then worked up to afford an oil, which is dissolved in ethanol, treated with 40% aqueous potassium hydroxide, and heated at 95° for 9 hours. The reaction mixture is then poured into aqueous sodium dihydrogen phosphate and extracted with ethyl acetate. Evaporation affords meteneprost free acid as a yellow oil, homogeneous by TLC. To insure homogeneity, the material is then chromatographed. The resulting colorless oil is then dissolved in methanol, treated with 0.5 equivalents of potassium carbonate, concentrated, and the residue crystallized from methanol/hexane/THF to afford meteneprost potassium salt as a white, free-flowing powder. By HPLC, this material is 98.0% pure, and contains less than 0.2% of the undesired 5,6-trans isomer. This procedure is set forth in Example 14A. An alternate, less preferred procedure is set forth in Example 14.

Other prostaglandins of commercial value can also be prepared from intermediates A-6A, A-4A, and A-7A provided by this process. For example prostaglandin $F_{2\alpha}$, which is used for synchronization of estrus in cattle, can be obtained by treating the cyclized sulfone of formula A-11 with lithium diisopropylamide in THF, followed successively by acetone, sodium amalgam, periodic acid, the potassium salt of 2-keto-heptyl-dimethylphosphonate, sodium periodate in the presence of a catalytic amount of osmium tetroxide, DIBAL/BHT reagent, potassium cyanide in aqueous dimethylsulfoxide (DMSO), and finally potassium hydroxide.

The preparation of the intermediates ecompassed within the scope of generic formulas A-5A, A-6A, and A-7A is accomplished by analogous procedures well known in the art.

Thus, carboxylic acid salts of the formula A-5A (wherein $R_1$ is $-CO_2M$, and $R_2$ and $R_3$ are $-CH_3$) are prepared by saponification of ester A-5. Amides A-5A (wherein $R_1$ is $CONHR_2$ or $CON(R_2)_2$) are then prepared by treating the carboxylic acid salt A-5A first with oxalyl chloride then with an amine. Nitrile A-5A (wherein $R_1$ is CN and $R_2$ and $R_3$ are $-CH_3$) is prepared by condensing compound A-3 with diethylcyanomethyl phosphonate, then hydrogenating over a palladium catalyst (see, Ohrui, H. and Kuzuhara, H., Agr. Biol. Chem. 44:907 (1980) for an example of this process). Imines of A-5A (wherein $R_1$ is $CHNR_2$), oximes of A-5A (wherein $R_1$ is CHNOR), and hydrazones of A-5A (wherein $R_1$ is $CHNN(R_2)_2$) are then prepared by reducing the nitrile A-5A (wherein $R_1$ is $-CN$) to the corresponding aldehyde (using, for example, diisobutylaluminum hydride), then treating the aldehyde with either a primary amine, hydroxylamine, o-alkyl hydroxylamine, hydrazine, or substituted hydrazine.

Acetals and ketals of A-5A (wherein $R_2$ is not $CH_3$) are prepared by condensing glucose with the appropriate ketone or aldehyde, followed by oxidation to the corresponding ketone, followed by condensation with $R_1CH_2PO(OCH_3)_2$, followed by catalytic hydrogenation. For example, compound A-5A (wherein $R_1$ is $CO_2CH_2CH_3$, $R_2$ and $R_3$ are $(CH_2)_5$) can be prepared by condensing glucose with cyclohexanone (see Hockett, et al., J. Amer. Chem. Soc. 71:3072 (1949)), followed by oxidation (see Tweit, et al., Carb. Res. 84:175 (1980)), followed by condensation with triethylphosphono-acetate, followed by catalytic hydrogenation.

The compounds of formula A-5A are then converted into compounds of formula A-6A by the method of this invention, viz, treatment with a non-nucleophilic strong base such as lithium hexamethyldisilazide followed by an alkylating agent of the generic formula $BrA_1$-$R_4$.

Compounds of the formula A-6A into compounds of the formula A-7A by successive treatments with aqueous ethanolic acid, sodium periodate, and sodium borohydride.

Compounds of the formula A-7A are converted into compounds of the formula A-10A by methods well known to those skilled in the art of organic synthesis. For instance, protected cyanohydrin-tosylate of the formula A-10A (wherein $R_5$ is $OSO_2C_6H_5pCH_3$, and W is $CH_3CH(OCH_2CH_3)$, CN) is prepared by successive treatments of the compound of formula A-7A with tosyl chloride, diisobutyl aluminum hydride, pyridinium chlorochromate, sodium cyanide, and ethyl vinyl ether. The nitro tosylate of the formula A-10A (wherein $R_5$ is $OSO_2C_6H_5pCH_3$, and W is H, $NO_2$) is prepared by successive treatments of the formula A-7A compound with tosyl chloride, diisobutyl aluminum hydride, triphenylphosphine/iodine/imidazole reagent, and silver nitrite. The thio acetal-tosylate of the formula A-10A (wherein $R_5$ is $OSO_2C_6H_5pCH_3$, and W is $-SCH_2CH_3$, $-SCH_2CH_3$) is prepared by successive treatments of A-7A with tosyl chloride, diisobutyl aluminum hydride, pyridinium chlorochromate, and methylthio-trimethylsilane (see Evans, et al., J. Amer. Chem. Soc. 97:3229 (1975)). The phosphine-oxide-chloride of the formula A-10A (wherein $R_5$ is Cl, W is H, $PO(C_6H_5)_2$) is prepared by successive treatments of A-7A with methane sulfonyl chloride in DMF (85° C., 2.0 hours), lithium aluminum hydride (THF, 0° C., 10 minutes), triphenylphosphine/iodine/imidazole reagent (in toluene at room temperature for 30 mimutes), then diphenylphosphine oxide (see Hunt, et al., J. Chem. Soc. 2413 (1975)) and sodium hydride in DMF (room temp, 1.0 hour). The chloro-triphenylphosphonium iodide of the formula A-10A ($R_5$ is Cl, W is H, $(C_6H_5)_3PI$) is prepared by successive treatments of A-7A with methane sulfonyl chloride in DMF, lithium aluminum hydride, triphenyl phospine/iodine/imidazole reagent, and triphenylphospine. The chloro-sulfoxide of the formula A-10A (wherein $R_5$ is Cl, W is H, $-SOC_6H_5$) is prepared by successive treatments of A-7A with methane sulfonyl chloride in DMF, lithium aluminum hydride, triphenyl phosphine/iodine/imidazole reagent, sodium-thiophenoxide, and sodium periodate. The chloro-sulfone of the formula A-10A (wherein $R_5$ is Cl, and W is H, $SO_2CH_3$) is prepared by successive treatments of A-7A with methane sulfonyl chloride in DMF, lithium aluminum hydride, triphenylphosphine/iodide/imidazole reagent, sodium methyl mercaptide (methanol, room temperature for 30 min) and m-chloroperbenzoic acid (methylene chloride, $-20°$ C., 1.5 hours).

Compounds of the formula A-10A are then converted into compounds of the formula A-11A by treatment with strong bases such as lithium, sodium or potassium hexamethyldisilazane, lithium diisopropyl amide, potassium t-butoxide and the like.

The compound of the formula A-11A (wherein W is H, $SO_2CH_3$; $A_1$ is cis-$CH_2CHCH(CH_2)_3$; $R_2$ and $R_3$ are $CH_3$; and $R_4$ is Cl) is converted into meteneprost precursor A-12 by treatment with potassium t-butoxide and iodine in THF (0° C., 15 minutes). The compound of the formula A-11A (wherein W is $P(C_6H_5)_3$, $A_1$ is cis $CH_2CHCH(CH_2)_3$, $R_2$ and $R_3$ are $CH_3$, and $R_4$ is Cl) is converted into meteneprost precursor A-12 by treatment with paraformaldehyde in THF. The compounds of the formula A-11A (wherein W is H, $SOC_6H_5$, or H, $PO(C_6H_5)_2$; $A_1$ is cis-$CH_2CHOH(CH_2)_3$; $R_2$ and $R_3$ are $CH_3$; and $R_4$ is Cl) are converted into meteneprost precursor A-12 by the methods described above, e.g., successive treatments with n-butyllithium, diisopropyl amine, iodomethyltributyltin, and n-butyllithium.

Compounds of the formula A-11A (wherein W is $CH_3CH(OCH_2CH_3)O$, CN; $CH_3S$, $CH_3S$; and H, $NO_2$; $A_1$ is cis $CH_2CH=CH(CH_2)_3$; $R_2$ and $R_3$ are $CH_3$ and $R_4$ is Cl) are useful precursors not only of meteneprost but also E and F series prostaglandins. Thus the compound of the formula A-11A (wherein W is $CH_3CH(OCH_2CH_3)O$; CN; $A_1$ is cis $CH_2CHCH(CH_2)_3$; $R_2$ and $R_3$ are $CH_3$; and $R_4$ is Cl) is converted into $PGF_{2\alpha}$ (formula D-6) by treatment with the following reagents in succession: periodic acid, dimethyl-2-oxo-heptylphosphonate, DIBAL/BHT reagent, aqueous sulfuric acid, lithium tri-sec-butylborohydride, potassium cyanide, and potassium hydroxide, (see Stork, et al., J. Amer. Chem. Soc. 100:8272 (1978)). The compound of the formula A-11A (wherein W is H, $NO_2$; $A_1$ is cis $CH_2CHCH(CH_2)_3$; $R_2$ and $R_3$ are $CH_3$; $R_4$ is Cl) is converted into $PGE_2$ (formula G-5) by treatment with the following reagents in succession; periodic acid, dimethyl-2-oxo-heptylphosphonate, DIBAL/BHT reagent, potassium cyanide, potassium hydroxide, and titanium trichloride (see McMurray, et al., J. Amer. Chem. Soc. 93:5309 (1971)). The compound of the formula A-11A (wherein W is $CH_3S$, $CH_3S$; $A_1$ is $cisCH_2CHCH(CH_2)_3$; $R_2$ and $R_3$ are $CH_3$; and $R_4$ is Cl) is converted into $PGF_{2\alpha}$ by treatment with the following reagents in succession: aqueous sulfuric acid, sodium borohydride, mercuric chloride and calcium carbonate in aqueous acetonitrile, DIBAL/BHT reagent, sodium periodate, dimethyl-2-oxo-heptylphosphonate, DIBAL/BHT reagent, potassium cyanide, and potassium hydroxide. Methods for preparing $PGF_{2\alpha}$ and $PGE_2$ are depicted in Charts D, E, F, and G.

The preparation of pyridinium chlorochromate (PCC) is described in Corey, et. al., Tet. Lett. 2647 (1975).

The Emmons reagent (ethyl dimethylphosphonoacetate) is prepared as follows. An equimolar mixture of ethyl bromo-acetate and trimethylphosphite is heated until evolution of methyl bromide begins (approximately 100° C.). After the evolution of methyl bromide ceases, the reaction mixture is vacuum distilled (118°–120° C./1.5 mm) to afford the Emmons reagent as a colorless liquid in pure form.

The alpha chain bromide (formula B-4) is prepared as set forth in Chart B. In step 1, a solution of lithium amide in liquid ammonia is treated with a solution of propargyl alcohol in dry THF, followed by a solution of 1,3-bromo-chloro-propane in THF. Both additions are exothermic, so they must be done slowly with efficient cooling. When the last of the 1,3-bromo-chloro-propane solution has been added, the reaction mixture is allowed to reflux for 20 minutes to insure completeness, then worked-up to afford an orange-red oil.

For the hydrogenation (step 2), the hydrogenation catalyst is prepared in situ by treating a cooled (0° C.) solution of nickel acetate tetrahydrate in 95% ethanol with a solution of sodium borohydride in absolute ethanol and then deactivated by adding ethylenediamine. The alkylated propargyl alcohol is then added and the reaction mixture stirred under 50 psi $H_2$. Uptake of $H_2$ is rapid at first, then slows, but does not cease, at one equivalent. It is not necessary to stop the hydrogenation after uptake of exactly one equivalent of $H_2$, because the fully saturated bromide does not react with the lithium derivative of the hydrogenated ester (A-5) as rapidly as does the alpha chain bromide (B-4). Thus, overhydrogenation can be allowed to take place. The reaction mixture is then worked up in the usual manner to afford a yellow-brown oil, which is dissolved (140° pot temperature/12 mm) to afford a light yellow oil, identified as the indicated cyclic alcohol by $^1H$-NMR. The cis-trans ratio is 98.8/1.2 by capillary gas chromatography (GC).

Finally, in step 3, the cis-allylic alcohol is covered with a saturated hydrocarbon solvent such as heptane, cooled to 0° C., and treated with slightly more than the theoretical amount of $PBr_3$. After 1 hour, the organic layer is washed consecutively with water and aqueous sodium bicarbonate, then concentrated to a yellow liquid, identified as the indicated alpha chain bromide by $^1H$-NMR. The cis/trans ratio is 98.6/1.4 by GC. This preferred procedure is set forth in preparations 1A, 2A, and 3A. An alternate, less preferred procedure is set forth in preparations 1, 2, and 3.

The preparation of the tin reagent is described in Still, J. Amer. Chem. Soc. 100:1481 (1978). Zinc-copper couple is prepared by adding granular zinc to a hot (100° C.) solution of cupric acetate monohydrate in acetic acid (HOAc), then decanting the HOAc and rinsing off the last traces of HOAc with ether. The couple is then covered with dry THF and treated with a solution of methylene iodide in THF at a rate such that the internal temperature does not exceed 40° C. When the addition is complete, neat tributyltin chloride is added all at once and the reaction mixture stirred at room temperature for 18 hours. (A shorter reaction time may suffice). The reaction mixture is then worked up to afford the tin product in slightly impure form as a colorless liquid. This liquid is then vacuum distilled (128°–147° C./0.85 mm), and then chromatographed. This reagent can be stored at room temperature in an unsealed container for an indefinite time.

The preparation of the beta-chain phosphonate is described in U.S. Pat. No. 4,060,534, which is incorporated herein by reference. Other beta chain phosphonates are also prepared as described therein.

While the intermediate of the formula A-6 and the process disclosed herein may be used to make a variety of prostaglandins meteneprost is the most preferred compound to be prepared by this invention.

DESCRIPTION OF THE PREFERRED EMBODIMENTS

The operation of the present invention is seen more fully by the Examples given below.

Preparation 1

Alpha chain acetylene

Refer to Chart B (conversion of B-1 to B-2).

A solution of anhydrous ferric chloride (0.168 g) in liquid ammonia (approximately 2.5 l) is treated with lithium rod (41.77 g, 5.967 moles) piece by piece over a period of 40 min. The resulting dark blue solution is then stirred at reflux until formation of $LiNH_2$ is complete as evidenced by disappearance of the blue color and appearance of a white precipitate (2 hr are required). The reaction mixture (a thin slurry) is then treated with a solution of propargyl alcohol (167.1 g, 2.984 moles) in 300 ml THF. Some heat is evolved, which causes the ammonia to reflux briskly. To keep the refluxing under control, the flask is immersed periodically in a dry ice/acetone bath. The addition requires 30 min. The reaction mixture (a gray-white slurry) is kept at reflux for 30 min and subsequently treated with a solution of 1-bromo-3-chloro-propane (480.67 g, 3.052 moles) in 150 ml THF. As before, heat is evolved. To keep the ammonia from refluxing too vigorously, either the reaction vessel is immersed in a dry ice/acetone bath or the rate of addition of the bromo-chloro-propane solution is moderated. The addition requires 35 min. The reaction mixture (still a gray slurry) is then stirred at reflux for 30 min and quenched with solid ammonium chloride (192 g, 3.59 moles: added in portions, with cooling). The condenser is then removed to allow the ammonia to evaporate. After 16 hrs, the bulk of the ammonia has evaporated. The last traces are then removed by immersing the flask in a lukewarm water bath, followed by applying steam to the bottom of the flask. The solid residue is then dissolved in 1 l of water, extracted with technical grade methylene chloride (3×500 ml), dried ($MgSO_4$), and concentrated in vacuo to yield a red-orange liquid. The volume is approximately 450 ml. This liquid is then vacuum distilled through an 8″ Vigreaux (96°–102° C./2.0–2.2 mm) to afford a colorless liquid.

Preparation 2

Semi-hydrogenation of alpha chain acetylene to cis-allylic alcohol

Refer to Chart B (conversion of B-2 to B-3).

A suspension of powdered nickel acetate tetrahydrate (9.950 g, 39.96 mmoles) in 320 ml 95% ethanol is stirred at room temperature until all the solids are dissolved (approximately 1 hr). This solution is then cooled to 0° C. and treated with solid sodium borohydride (1.51 g, 39.7 mmoles), which causes a fine black solid to precipitate instantaneously. This catalyst is then deactivated by addition of neat ethylene diamine (8.228 g, 137.1 mmoles). A solution of the alpha chain acetylene (Preparation 1, 53.04 g, 0.4003 moles) in 80 ml absolute ethanol is then added, and the reaction mixture is placed in a Parr shaker under 60 psi hydrogen. The pressure drops steadily to 32 psi over a period of 48 min, then remains constant over the next two hours. The catalyst is then filtered off through a pad of Darco G-60 atop a pad of celite 545. The filtrate (purple-colored) is then concentrated in vacuo to a purple semi-solid, which is taken up in 500 ml water, extracted three times with 500 ml portions of technical grade ethyl acetate, dried over magensium sulfate, and concentrated in vacuo to a colorless oil.

Preparation 3

Conversion of cis-allylic alcohol into alpha chain bromide

Refer to Chart B (conversion of B-3 to B-4).

A solution of the cis-allylic alcohol (Preparation 2, 54.0 g, 0.4015 moles) in 340 ml heptane is cooled to 0° C. and then treated with a solution of $PBr_3$ (21.5 ml, 61.32 g, 0.2265 moles) in 240 ml heptane (added dropwise over a period of 10 min). The reaction mixture is then stirred at 0° C. for 3.5 hrs and poured into 400 ml water. The two phases are vigorously mixed and then the aqueous layer is then separated and the heptane layer washed with 400 ml 5% sodium bicarbonate, dried ($MgSO_4$), and concentrated in vacuo to leave a colorless liquid, which is distilled through a 3" Vigreaux (70°–73° C./1.5 mm) to afford a pale yellow liquid.

Preparation 1A

Alpha chain acetylene

Refer to Chart B (conversion of B-1 to B-2).

A solution of lithium amide (7.77 kg, 337.8 moles) in 285 liters of ammonia is cooled to −40° C. and treated with propargyl alcohol (9.35 kg, 167.0 moles) over a period of 30 minutes. The reaction mixture is then stirred at reflux for 1 day, then treated with 1-bromo-3-chloro-propane (24.1 kg, 153.0 moles). After the addition is complete, the reaction mixture is stirred at reflux for 20 minutes, then quenched with ammonium chloride (11.0 kg, 205.6 moles). The bulk of the ammonia is then allowed to evaporate to leave a semi-solid residue, which is taken up in 200 l of water, extracted with semi-solid residue, which is taken up in 200 l of water, extracted with methylene chloride (3×33 l), and concentrated in vacuo to leave an orange-red oil, identified as the title compound by $^1$H-NMR.

Preparation 2A

Semi-hydrogenation of alpha chain acetylene to cis-allylic alcohol

Refer to Chart B (conversion of B-2 to B-3).

The alpha chain acetylene (14.92 kg) is divided into two equal lots, and each is semi-hydrogenated by the following procedure. A solution of nickel acetate tetrahydrate (1.56 kg, 6.27 moles) in 45.7 kg 95% ethanol is treated with solid sodium borohydride (227 g, 5.97 moles), which causes a fine black solid to precipitate instantaneously. This catalyst is then deactivated by addition of neat ethylenediamine (1.37 l, 20.5 moles). The alpha chain acetylene (7.60 kg, 57.4 moles) is then added, and the reaction mixture is placed in a reactor under an atmosphere of hydrogen gas (40 psi). When slightly over the theoretical amount of hydrogen gas has been absorbed, the reaction mixture is filtered through 1.5 kg solka floc, which is rinsed with 12 l 95% ethanol. The filtrates from the two runs are then combined and concentrated to leave a purple slush (volume: ca. 12 l), which is then diluted with 30 l of water and extracted with ethyl acetate (2×20 l). The extracts are then concentrated in vacuo to leave a light yellow oil, which is distilled (140° C. [pot temperature]/12 mm) to afford a light yellow oil. By capillary GC, this material consists of a mixture of the title compound and the trans isomer in a 98.8/1.2 ratio.

Preparation 3A

Conversion of cis-allylic alcohol into alpha chain bromide

Refer to Chart B (conversion of B-3 to B-4).

A suspension of the cis-allylic alcohol (8.90 kg, 66.2 moles) in 50.8 l heptane is cooled to 0° C., then treated with neat phosphorus tribromide (9.80 kg, 36.2 moles). The rate of addition is controlled so that the temperature does not rise about 0° C. (23 minutes). The reaction mixture is then stirred at 0° C. for 1 hour, then quenched with 18.2 l water, which causes the temperature to rise to 18°. The aqueous layer is then separated and extracted with 15 l heptane. The two heptane solutions are then combined, washed successively with 18.5 l 5% sodium bicarbonate and 10 l saturated sodium chloride, and concentrated in vacuo to leave a yellow oil, composed of a mixture of the title compound, the corresponding trans isomer, and 3-bromo-6-chloro-1-hexene (ratio: 94.8/1.3/3.9) by capillary GC.

Preparation 4

Lithium hexamethyldisilazide

A solution of n-butyllithium in hexane (1.55M, 390 ml, 0.605 moles) is cooled to 0° C. and treated dropwise over a period of 15 min with neat hexamethyldisilazane (118.12 g, 0.7337 moles). The resulting yellow solution is then refluxed for 1.5 hr, and concentrated in vacuo to yield a white solid residue. To remove the excess hexamethyldisilazane, this residue is dissolved in heptane, and the heptane is removed in vacuo. The material is then tumble-dried (50° C./2 mm/30 min). The final product is a white solid with a melting point of 70°–83° C.

Preparation 5

Preparation of Emmons' Reagent

A neat mixture of ethyl bromoacetate (80.0 g, 0.4790 moles) and trimethylphosphite (57.0 ml, 60.0 g, 0.4839 moles) is heated to 130° C. (bath temperature), at which point the reaction mixture begins to reflux extremely vigorously. When the reflux subsides, more trimethylphosphite (15 ml) is added, again causing the reaction mixture to reflux briskly. After 2 min, the reflux subsides. The reaction mixture is then heated at 140°–150° C. for 2.5 hr, and subsequently vaccum distilled (1.5 mm) through a 6″ Vigreaux. A sizeable fore-run (50°–100° C.), consisting mostly of methyl dimethylphosphonate by $^1$H-NMR, is first collected. The main fraction (118°–120° C.), a colorless liquid consisting of ethyl dimethylphosphonoacetate in nearly pure form by $^1$H-NMR, is then collected.

Preparation 6

Preparation of Benzyltrimethylammonium p-toluene-sulfinate

A solution of p-toluene-sulfinic acid, sodium salt dihydrate (21.417 g, 0.1001 moles) in 100 ml of water is covered with 100 ml of ethyl acetate and treated dropwise with concentrated sulfuric acid (neat; 13.26 g, 0.1353 moles). When the addition is complete (10 min), the aqueous layer is separated and the organic layer is washed with 150 ml 2.0M sodium chloride, and then dried over magnesium sulfate. This solution, containing p-toluene-sulfinic acid, is then neutralized with benzyltrimethylammonium methoxide (50.496 g of a 40% solution in methanol, 20.198 g, 0.1116 moles). The resulting clear yellow solution is then stirred at room temperature for 30 min, and concentrated in vacuo to leave a yellow oil. The last traces of methanol are then removed by four azeotropic distillations with methylene chloride followed by vacuum drying (40° C. 2 mm, 1 hr). The residue left after these operations is a free-flowing, pale yellow powder. This powder was identified as the title compound in completely pure form by $^1$H-NMR.

Preparation 7

Preparation of Iodomethyltributyl-tin

A hot (100° C.) solution of cupric acetate hydrate (0.1507 g, 0.7548 mmoles) in 15 ml glacial acetic acid is treated with zinc metal (30 mesh; 9.8004 g, 0.1499 moles), stirred for 2 min and the acetic acid (containing zinc acetate) then decanted. Another 15 ml portion of acetic acid is then added and the slurry again stirred at 100° C. for 2 min. The acetic acid is then again decanted and the last traces of acetic acid removed by trituration three times with 30 ml portions of anhydrous ether. The residual red-brown powder is then covered with 20 ml THF and treated with several drops of a solution of $CH_2I_2$ (40.269 g, 0.1503 moles) in 20 ml THF. When the reaction mixture becomes purple (indicating that formation of iodomethylzinc-iodide has begun), the reaction mixture is diluted with 60 ml THF and treated dropwise with the remainder of the $CH_2I_2$ solution. During this addition, the reaction flask is periodically immersed in an ice-water bath to prevent the internal temperature from rising about 43° C. and thereby minimize the amount of decomposition of iodomethylzinc iodide. After the addition is complete (1.5 hr), the reaction mixture is stirred at 40° C. for 30 min, then cooled to 5° C. and filtered through a funnel with a coarse porosity frit. The purple filtrate is then treated dropwise (over a period of 15 min) with tributyltin chloride (32.356 g, 99.56 mmoles). During this attention, the temperature of the reaction mixture rises to 31° C. The reaction mixture is then stirred at room temperature for 17.5 hrs, diluted with 300 ml of hexane, washed twice with 200 ml portions of water, dried over magnesium sulfate, and concentrated in vacuo to leave a yellow oil weighing 44.30 g. This oil is then vacuum distilled (120°–147° C./0.85 mm) through a short-path to afford a colorless liquid weighing 41.524 g. By gas chromatography this material is only 75.1% pure. Identified impurities include $nBu_3SnI$ (3.8%), $nBu_2Sn(CH_2I)_2$ (1.9%), $nBu_3SnCH_3$ (0.7%), $nBu_3SnCl$ (0.4%), and $nBu_4Sn$ (0.1%). By TLC (eluant: hexane), this material consists of one major component (Rf=0.73) and three minor components (Rf=0.82, 0.59, and 0.00 to 0.20). A 29.0 g portion of this oil is then chromatographed on 500 g silica gel (eluant, hexane; fraction size, 100 ml). Fraction 3, consisting of a mixture of the components of Rf=0.82 and 0.73, is concentrated in vacuo to leave a colorless oil consisting of a mixture of $nBu_3SnCH_3$ (66.2%), $nBu_4Sn$ (12.5%), and $nBu_3SnCH_2I$ (21.4%) by GC. Fractions 4–8 are then pooled and concentrated in vacuo to leave a colorless oil identified as $nBu_3SnCH_2I$ by GC (98.8% pure; this material is completely uncontaminated by $nBu_3SnI$ and $nBu_2Sn(CH_2I)_2$, and contaminated by only small amounts of of $nBu_3SnCH_3$ (1.4) and $nBu_4Sn$ (0.3%). The fractions containing the component of Rf=0.59 (10–14) are then pooled and concentrated in vacuo to leave a colorless oil By GC, this oil consists of a mixture of $nBu_2Sn(CH_2I)_2$ (90.0%) and $nBu_3SnCH_2I$ (10.1%).

EXAMPLE 1

Conversion of D-glucose (A-1) into diacetone-glucose (A-2)

Refer to Chart A, Step 1.

This is a variant of the procedure described in Schmidt, O.T. Meth. Carb. Chem. 2:318 (1962).

A suspension of D-glucose (450.0 g, 2.50 moles) in technical grade acetone (3.0 l) is treated with anhydrous granular zinc chloride (Mallinckrodt technical grade, 369.0 g, 2.708 moles), followed by 85% phosphoric acid (22.5 ml). The temperature rises to 35°, then gradually settles back down to room temperature. The reaction mixture is then stirred at room temperature for 42 hrs. The unreacted glucose is then filtered off and washed thoroughly with technical grade acetone. The filtrate (orange colored) is then cooled to approximately 5° C. and treated with 50% sodium hydroxide until the mixture is slightly alkaline (amount added: 520 g). The temperature is never permitted to exceed 25° because, at higher temperatures, a significant amount of the product hydrolyzes to monoacetone-glucose. A white solid (presumably a mixture of zinc hydroxide and sodium chloride) gradually precipitates during the addition. When the addition is complete, this is filtered off and washed thoroughly with technical grade acetone. The filtrate is then concentrated in vacuo to leave a cloudly gold oil, which is diluted with 500 ml water and extracted with technical methylene chloride (4×500 ml). The combined extracts are then washed with 500 ml water and dried over $MgSO_4$. This solution, is used in Example 2.

EXAMPLE 2

Oxidation of Diacetone-glucose (A-2) to diacetone-glucose-ketone (A-3)

Refer tp Chart A, Step 2.

This is a variant of the procedure described in Herscovici, J., Antonakis, K., J. Chem. Soc. Comm. 561 (1980).

The above solution of diacetone-glucose (295.46 g, 1.136 moles) in methylene chloride, stirred over 3 Angstrom molecular sieves (Davison, 8–12 mesh beads, 1.25 kg), is treated with powdered pyridinium chlorochromate (PCC) (806.3 g, 3.740 moles). As the reaction proceeds, chromium salts deposit on the surface of the molecular sieves, causing them to clump together, which renders stirring increasingly difficult. After 28 hrs, the mechanical stirrer stops. The reaction mixture is allowed to stand at room temperature for another 14 hrs and then the supernatant is filtered through celite. The dark green, sticky mass remaining in the flask is triturated as thoroughly as possible with methylene chloride and then filtered through celite. A significant amount of PCC and/or reduced chromium salts are present in the filtrate along with the desired product. To separate them the methylene chloride is removed by distillation at atmospheric pressure and replaced with heptane, which causes them to precipitate (as a sticky oil which eventually changes to a hard, brittle solid). The mixture is then filtered hot through celite. A small amount of chromium salts which remain in the pot are triturated with boiling heptane (1 l) and again filtered. The combined filtrates are then concentrated in vacuo to leave a green oil.

EXAMPLE 3

Conversion of diacetone-glucose-ketone A-3 into unsaturated ester A-4

Refer to Chart A, Step 3.

A suspension of the potassium salt of ethyl dimethylphosphonoacetate in toluene is prepared by adding a solution of ethyl dimethylphosphonoacetate (117.67 g, 0.6004 moles) in 150 ml toluene to a cold (5° C.) suspension of potassium tert-butoxide (62.22 g, 0.5555 moles) in 950 ml toluene. The heat of reaction causes the temperature to rise to 15° C. To ensure that all of the potassium tert-butoxide has been consumed, the slurry is stirred at room temperature for 30 min. The reaction mixture is then cooled to −20° C. and treated with a solution of diacetone-glucose-ketone (Example 2, 130.93 g, 0.5075 moles) in 400 ml toluene (added over a period of 2 min). The heat of reaction causes the internal temperature to rise to +10° C. The reaction mixture (orange-colored and still heterogeneous) is then re-cooled to −20° C. and stirred at that temperature for 2.5 hrs (to ensure that all of the diacetone-glucose-ketone will be consumed). The reaction mixture is then quenched with 1 l 5% potassium hydroxide and the organic layer separated. The aqueous layer (which appears to be slightly emulsified) is then extracted twice with one liter portions of technical grade ethyl acetate. The two phases separate cleanly. The combined organic extracts are then washed with 1 liter saturated sodium chloride, dried over magnesium sulfate, and concentrated in vacuo to leave a pale yellow oil.

EXAMPLE 4

Catalytic hydrogenation of unsaturated ester A-4

Refer to Chart A, Step 4.

A solution of the crude unsaturated ester of Example 3 (159.8 g, 0.4872 moles) in 1 liter of absolute ethanol is buffered with a solution of $Na_2HPO_4$ (0.9805 g) in 50 ml of water. The resulting slightly hazy solution is then treated with 3.25 g 10% Pd/C and placed in a Parr shaker under 50 psi hydrogen. The pressure drops steadily to 26.5 psi over a period of 30 min, then remains approximately constant over the next two hours. The catalyst is then filtered off through a pad of solka floc and the filtrate concentrated in vacuo to a pale yellow oil, which is partitioned between 500 ml methylene chloride (technical grade) and 500 ml water. The methylene chloride layer is then separated and the aqueous layer is extracted with another 500 ml portion of methylene chloride. The combined methylene chloride extracts are then washed with 500 ml saturated sodium chloride, dried over magnesium sulfate, and concentrated in vacuo to yield a colorless oil which crystallizes on standing at room temperature (weight: 168.12 g). These crystals are dissolved in 320 ml boiling heptane and the solution allowed to cool to approximately 45° C. A seed is then added and crystallization begins immediately. The mixture is allowed to stand at room temperature for 20 hrs, and the crystals (white needles, with a melting point of 87°–89° C.) are filtered, washed sparingly with cold (−20° C.) heptane, and air-dried. The mother liquor is then concentrated in vacuo to yield an oil. A second crop is obtained by recrystallizing this oil from 50 ml boiling heptane. Third and fourth crops are then taken.

EXAMPLE 5

Alkylation of hydrogenated ester with alpha chain bromide

Refer to Chart A, Step 5 (conversion of A-4 to A-5).

A solution of lithium hexamethyldisilazide (23.75 g, 0.1422 moles) in 210 ml of THF is cooled to −25° C., and treated with a solution of the hydrogenated ester of Example 4 (33.07 g, 0.1002 moles) in 140 ml THF (added over a period of 1 min), which causes the internal temperature to rise to −12° C. The reaction mixture (orange-colored) is then re-cooled to −20° C. over a period of 5 min, then treated with the alpha chain bromide (Preparation 3, neat, 29.74 g, 0.1506 moles), which causes the internal temperature to rise to 0° C. The alpha chain bromide that remains on the walls of the addition funnel is then rinsed into the reaction mixture with 30 ml THF. The reaction mixture is maintained at 0° C. Ten minutes after the addition is complete, a TLC plate is spotted with the reaction mixture, eluted with 1:1 ethyl acetate/cyclohexane, and then charred with sulfuric acid. This TLC reveals that the reaction is complete (only two spots are visible, one corresponding to the desired titled alkylated ester [$R_f$=0.56] and the other corresponding to unreacted alpha chain bromide [$R_f$=0.63]. There is no spot at $R_f$=0.51, which corresponds to the starting hydrogenated ester. The reaction mixture is then quenched with a solution of $Na_2HPO_4$ (14.202 g, 0.1000 moles) in 100 ml water and allowed to warm to room temperature. To remove the unreacted alpha chain bromide, triethylamine (42 ml, 30.49 g, 0.3019 moles) is added and the reaction mixture stirred at room temperature. After 3 hrs, TLC indicates that the alpha chain bromide is almost completely absent, so the reaction mixture is then poured into 1 liter of 5% citric acid and extracted twice with 1 liter portions of ether. The extracts are then dried over magnesium sulfate and concentrated in vacuo to leave a yellow-orange oil.

EXAMPLE 6

Conversion of the alkylated ester into the hydroxyester

Refer to Chart A, Step 6 (conversion of A-5 to A-6).

A solution of the crude alkylated ester of Example 5 (44.74 g, 0.1002 moles) in 300 ml absolute ethanol is treated with dilute aqueous sulfuric acid (30 ml of 0.15M solution, 4.50 mmoles) and stirred at 70° C. until TLC (eluant: 1:1 ethyl acetate/cyclohexane) indicates that the hydrolysis has reached the end-point (about 5 hrs). The reaction mixture is then allowed to cool to room temperature, and treated with sodium bicarbonate (60 ml of 5% solution, 3.00 g, 35.7 mmoles) and $NaIO_4$ (23.554 g, 0.1101 moles). The reaction mixture is then diluted with 210 ml water and stirred at room temperature. After 30 min, the cleavage of the diol to the corresponding aldehyde [$R_f$=0.35] is complete. The reaction mixture (a thick, cream colored slurry) is cooled to 0° C. and treated with solid sodium borohydride (6.381 g, 0.1679 moles). The reaction mixture is then stirred at 0° C. for 30 min and poured into 1 l saturated ammonium chloride and extracted 3 times with 1 liter portions of technical grade methylene chloride. The extracts are washed with 500 ml 1% sodium hydroxide. The resulting pale yellow solution is then dried over magnesium sulfate and concentrated in vacuo to leave a red-orange oil, which is almost completely homogeneous by TLC and $^1$H-NMR.

EXAMPLE 7

Chlorination of hydroxy-ester

Refer to Chart A, Step 7.

A solution of crude hydroxy-ester of Example 6 (26.60 g, 0.07065 moles) and mesyl chloride (11.5 ml, 17.02 g, 0.1486 moles) in 125 ml DMF is treated with anhydrous lithium chloride (9.180 g, 0.2160 moles) and then stirred at 85° C. and monitored by TLC (eluant: 30% EtOAc/cyclohexane). After 30 min, TLC indicates the presence of two major products ($R_f$=0.32 [the formate ester of the starting material] and $R_f$=0.49 [the chloro-ester]), along with a small amount of unreacted starting material ($R_f$=0.16). After 2 hrs, only the desired chloro-ester and a very small amount of a slightly more polar byproduct ($R_f$=0.38), are present. At this time, the reaction mixture is allowed to cool to room temperature and then diluted with 500 ml heptane and washed with 500 ml water. The aqueous wash is back-extracted with 500 ml heptane and then the combined heptane extracts are washed with 500 ml 5% sodium bicarbonate, dried over magnesium sulfate, and concentrated in vacuo to leave a dark red oil.

EXAMPLE 8

Reduction of chloro-ester to chloro-alcohol

Refer to Chart A, Step 8.

A suspension of lithium aluminum hydride (4.9965 g, 0.1315 moles) in 100 ml THF is cooled to 0° C. and treated dropwise over a period of 10 min with a solution of the crude chloro-ester of Example 7 (27.05 g, 0.06848 moles) in 100 ml THF. After the addition is complete, the reaction mixture is stirred at 0° C. for 10 min, then, while the temperature is held at 5° C., the excess lithium aluminum hydride is quenched, first with 5.0 ml water (added dropwise until vigorous evolution of hydrogen gas ceases, then in a steady stream), secondly with 5.0 ml 15% sodium hydroxide, and finally with 15.0 ml more water. The reaction mixture (an off-gray slurry) is then stirred at room temperature for 1 hr (to ensure adequate time for complete hydrolysis of the initially-formed aluminum salt-product complex), and treated with magnesium sulfate with continued stirring. After 10 min, the solids are filtered off and the filtrate is concentrated in vacuo to yield a light brown oil.

EXAMPLE 9

Conversion of Chloro-alcohol into Uncyclized Chloro Sulfone

Refer to Chart A, step 9.

A solution of the crude chloro-alcohol of Example 8 (5.0271 g, 14.24 mmoles) and triphenyl phosphine (6.0013 g, 22.91 mmoles) in 10 ml toluene is treated with imidazole (2.9141 g, 42.85 mmoles). The resulting pale yellow suspension is then treated dropwise with a solution of iodine (5.0647 g, 19.94 mmoles) in 15 ml toluene. As soon as each drop is added to the reaction mixture, the purple color indicative of free iodine disappears. After the addition is complete (10 min), the reaction mixture (a yellow-orange solution containing a gummy orange precipitate) is stirred at room temperature for 30 min and then diluted with 150 ml ethyl acetate, washed with 200 ml 3% sodium hydroxide, dried over magnesium sulfate, and concentrated in vacuo to leave a gold oil, consisting of a mixture of one major organic component (Rf=0.49) and several very minor ones along with triphenylphosphine (Rf=0.63) and triphenylphosphine oxide (Rf=0.04), by TLC (eluant: 30% ethyl acetate/cyclohexane). No starting chloroalcohol (Rf=0.24) is detectable.

The gold oil is dissolved in 75 ml toluene and treated with solid benzyltrimethylammonium p-toluene-sulfinate (6.5045 g, 21.33 mmols). The resulting slurry is then stirred at 80° C. until TLC indicates that the Rf=0.49 component is completely consumed (2.5 hrs), then diluted with ethyl acetate, washed with 3% sodium hydroxide, dried over magnesium sulfate, and concentrated in vacuo to leave another gold oil, consisting of a mixture of one major organic component (Rf=0.28) and one minor one (Rf=0.36) in addition to triphenylphosphine and triphenylphosphine oxide by TLC. The ratio of the two organic components is estimated to be 90:10 by dividing the integral of the 8. Hz doublet at 7.80 ppm (belonging to the major component) by that of the 8. Hz doublet at 7.62 ppm (belonging to the minor component) in the $^1$H-NMR of the mixture.

This gold oil is chromatographed on 496 g silica gel (gradient elution: 20% to 30% ethyl acetate/cyclohexane; 100 ml fractions are collected). Fractions 7-9 are pooled and concentrated in vacuo to leave a colorless oil consisting of an approximately 1:1 mixture of the two organic products by TLC. This material is then rechromatographed to afford a small quantity of the minor organic product (Rf=0.36) as an oil, identified as the sulfite ester (presumably a mixture of diastereomers at sulfur) by $^1$H-NMR. The fractions containing only the major (Rf=0.28) organic product (nos 10–14) are then pooled and concentrated in vacuo to leave a colorless oil, identified as the uncyclized sulfone by $^1$H-NMR.

A small portion (170 mg) of this oil is dissolved in 2 ml boiling heptane containing 10 drops ethyl acetate, seeded, and allowed to cool to room temperature. The bulk of the material separates as an oil. However, over the next several hours, the size of the seed crystal grows visibly. After standing at room temperature for another six days, the bulk of the material has crystallized. The crystals are white prisms which melt sharply at 69°–71° C.

EXAMPLE 10

Conversion of Uncyclized Chloro Sulfone into Cyclized Sulfone

Refer to Chart A, step 10.

A solution of potassium t-butoxide (1.823 g, 16.28 mmoles) in 40 ml THF is cooled to −20°, and then treated with a solution of the uncyclized sulfone of Example 9 (4.0497 g, 8.248 mmoles) in 40 ml THF. After 30 min, the reaction mixture is poured into 150 ml 3% sodium hydroxide and extracted with methylene chloride (2×150 ml). The extracts are then dried over magnesium sulfate and concentrated in vacuo to leave a yellow oil. This oil is then dissolved in 50 ml boiling cyclohexane and seeded. A large mass of crystals separates while the solution is still hot. To insure that crystallization is complete, the mixture is allowed to stand at room temperature for 19 hrs. The crystals are then filtered off, triturated twice with cyclohexane, and dried in vacuo. The crystals (white plates, with a melting point of 123°–124.5°) are identified as the cyclized sulfone in isomerically pure form by 200 MHz $^1$H-NMR, $^{13}$C-NMR, and by the sharpness of its melting point. Anal. Calcd. for $C_{23}H_{31}ClO_5S$: C, 60.71; H, 6.87; S, 7.05. Found: C, 60.83; H, 6.83; S, 6.92.

TLC analysis (eluant: 40% ethyl acetate/cyclohexane) of the mother liquor indicates the presence of more cyclized sulfone ($R_f$=0.35) together with two impurities (Rf=0.47 and 0.32). The solvent is removed in vacuo, then the residual oil chromatographed on silica gel (gradient elution, 20% to 40% ethyl acetate/cyclohexane; fraction size: 25 ml). Fractions 12–17 are pooled and concentrated in vacuo to leave a colorless oil identified as a 40:60 mixture of the uncyclized sulfone and an isomer. Fractions 21–24 are pooled, then concentrated in vacuo to leave a colorless oil, identified as the cyclized sulfone in pure form by TLC. Fractions 25–28 are then pooled and concentrated in vacuo to leave a colorless oil, consisting of a 30:70 mixture of the cyclized sulfone and the 5,6-trans isomer by $^{13}$C-NMR.

EXAMPLE 11

Conversion of Cyclized Sulfone into 9-Methylene-cyclo pentane

Refer to Chart A, step 11.

A solution of diisopropylamine (0.50 ml), 3.57 mmoles) in 6 ml THF is cooled to 0°, then treated with a solution of n-butyllithium in hexane (1.7 ml of 1.55M solution, 2.63 mmoles). After 5 min, this solution is cooled to −25° C., and then treated with a solution of the cyclized sulfone of Example 10 (799.8 mg, 1.760 mmoles) in 4.5 ml THF. The resulting yellow solution is then stirred at −25° C. for 40 min, and then treated with a solution of iodomethyltributyltin (Preparation 7; 985.8 mg, 2.289 mmoles) in 1.5 ml THF. The reaction mixture is then stirred at −25° C. until a TLC (eluant: 30% ethyl acetate/cyclohexane) indicates that conversion of the starting material (Rf=0.21) into a less polar component (Rf=0.48) is complete (2 hr). The reaction mixture is then poured into 50 ml 3% sodium hydroxide, extracted twice with 50 ml of ether, dried over magnesium sulfate, and concentrated in vacuo to leave a yellow oil (weight: 1.5172 g) identified as a mixture of the stannylated sulfone and iodomethyltributyl-tin (Rf=0.65) by TLC and $^1$H-NMR.

This yellow oil is then taken up in 10 ml THF, cooled to −78° C., and treated with CH$_3$Li.LiBr/Et$_2$O (2.5 ml of 1.4M solution, 3.50 mmoles). After 25 min, the reaction mixture is poured into 50 ml 3% sodium hydroxide, extracted twice with 50 ml portions of ether, dried over magnesium sulfate, and concentrated in vacuo to leave a yellow oil consisting of two major components (Rf=0.54 and 0.65) and several minor components by TLC. This oil is then chromatographed (gradient elution, 5% to 20% ethyl acetate/cyclohexane; fraction size, 20 ml). The fractions containing the component of Rf=0.54 are then pooled and concentrated in vacuo to leave a colorless oil, identified as the 9-methylene-cyclopentane by $^1$H-NMR.

EXAMPLE 11A

Conversion of cyclized sulfone into 9-methylene-cyclopentane.

Refer to Chart A, step 11.

A solution of the cyclized sulfone of Example 10 (10.011 g, 22.026 mmoles) in 90 ml THF is cooled to −78°, then treated over a period of 2 minutes with a solution of butyllithium in hexane 942.0 ml of 1.6M solution, 67.2 mmoles), during which time the internal temperature rises to −43° C. The resulting yellow reaction mixture is then re-cooled to −78° C. and treated with neat dibromomethane (6.2 ml, 15.357 g, 88.26 mmoles). Over the course of the addition (1 minute), the temperature rises steadily to −5° C. and the color changes from yellow to red brown. The reaction mixture is then stirred at 0° for 20 minutes, poured into 900 ml 3%, extracted with methylene chloride (3×600 ml), dried over magnesium sulfate, and concentrated to leave a red-brown oil, identified as the 9-methylene-cyclopentane in essentially pure form by 1N-NMR and TLC (eluant: 30% ethyl acetate/cyclohexane).

EXAMPLE 12

Conversion of 9-Methylene-cyclopentane into Chloroenone

Refer to Chart A, step 10.

A solution of the 9-methylene-cyclopentane of Example 11 (308.9 mg, 0.9885 mmoles) in 4 ml THF is treated with a solution of periodic acid dihydrate (455.5 mg, 1.998 mmoles) in 5 ml of water. The resulting hazy reaction mixture is then stirred at room temperature until TLC (eluant: 20% ethyl acetate/cyclohexane) indicates that conversion of the 9-methylene cyclopentane (Rf=0.45) into a more polar (Rf=0.16) component is complete (40 min).

The reaction mixture is then poured into 50 ml 0.1N Na$_2$HPO$_4$, extracted twice with 50 ml ethyl acetate, dried over magnesium sulfate, and the volume reduced to 5 ml by vacuum disillation. This solution is then diluted with 5 ml THF and added to a solution (bright yellow) of the potassium salt of the β-keto-phosphonate in THF, prepared 30 min in advance by treating a solution of dimethyl-2-keto-3,3-dimethyl-heptylphosphonate (455.5 mg, 1.782 mmoles) in 3 ml THF with a solution of potassium-tert-butoxide (180.7 mg, 1.613 mmoles) in 2 ml THF. The reaction mixture is then stirred at room temperature until TLC indicates that conversion of the component of Rf=0.16 into a less polar component (Rf=0.21) is complete (1 hr). The resulting viscous reaction mixture is then poured into 50 ml 3% sodium hydroxide, extracted twice with 50 ml portions of ethyl acetate, dried over magnesium sulfate, and concentrated in vacuo to leave a yellow oil identified as the title compound in nearly pure form by $^1$H-NMR and TLC.

EXAMPLE 12A

Conversion of 9-methylene-cyclopentane into chloroenone

Refer to Chart A, step 12.

A solution of the crude 9-methylene-cyclopentane of Example 11 (7.823 g) in 50 ml THF is treated with 15 ml water followed by a solution of periodic acid dihydrate (10.044 g, 44.05 mmoles) in 35 ml water. The resulting hazy solution is then stirred at room temperature until analysis by TLC (eluant: 30% ethyl acetate/cyclohexane) indicates that conversion of the 9-methylene-cyclopentane ($R_f$=0.57) into a more polant component ($R_f$=0.26) is complete (40 minutes). The reaction mixture is then poured into 900 ml 0.1M sodium dihydrogen phosphate/saturated sodium chloride, extracted with ethyl acetate (2×900 ml), dried over magnesium sulfate, and the volume reduced to approximately 20 ml by vacuum distillation. This solution is then added to a solution of the sodium salt of dimethyl-2-keto-3,3-domethyl-heptylphosphonate in THF, prepared 90 minutes in advance by treating a suspension of 99% sodium hydride (1.060 g, 44.17 mmoles) in 32 ml THF with a solution of the phosphonate (14.454 g, 57.82 mmoles) in 12 ml THF. The reaction mixture is then stirred at room temperature for 2 hours, then poured into 500 ml 3% NaOH, extracted with ethyl acetate (2×500 ml), dried over magnesium sulfate, and concentrated in vacuo to leave a red oil, identified as the title compound in essentially pure form by TLC ($R_f$=0.43) and $^1$H-NMR.

EXAMPLE 13

Conversion of Chloro-enone into Chloro-meteneprost

Refer to Chart A, step 13.

A solution of 3,5-di-t-butyl-4-hydroxy-toluene (1.3068 g, 5.940 mmoles) in 16 ml of toluene is cooled to 0° C., treated with a solution of diisobutylaluminum hydride (DIBAL) in toluene (3.4 ml of 1.47M solution, 5.00 mmoles), stirred at 0° for 1 hr, cooled to −78° C. and treated with a solution of the crude yellow oil of Example 12 (539.7 mg, containing approximately 0.8224 mmoles chloro-enone) in 2 ml toluene. The reaction mixture is then allowed to warm up to −5° C. and stirred until TLC (eluant: 20% ethyl acetate/cyclohexane) indicates that almost all of the chloro-enone (Rf=0.66) has been consumed (1 hr). The reaction mixture is then poured into 100 ml 5% HCl, extracted three times with 100 ml portions of methylene chloride, dried over magnesium sulfate, and concentrated in vacuo to leave a yellow oil consisting of a small amount of the chloro-enone (Rf=0.66), major amounts of two products (Rf=0.54 and 0.43), and trace amounts of several impurities. This yellow oil is then chromatographed on 150 g silica gel (gradient elution, 20% to 50% ethyl acetate/cyclohexane; fraction size 50 ml). The fractions containing the component of Rf=0.54 (16–18) are pooled and concentrated in vacuo to leave a colorless oil identified as the 15R isomer of the titled product.

The fractions containing the component of Rf=0.43 (21–27) are then pooled and concentrated in vacuo to leave a pale yellow oil, identified as chlorometeneprost by $^1$H-NMR.

EXAMPLE 13A

Conversion of chloro-enone into chloro-meteneprost

Refer to Chart A, step 13.

A solution of 3,5-di-t-butyl-4-hydroxy-toluene (38.30 g, 0.1741 moles) in 200 ml toluene is cooled to 0° C., treated with a solution of diisobutyl-aluminum hydride in toluene (103 ml of 1.47M solution, 0.1514 moles), stirred at 0° C. for one hour, then cooled to −46° and treated with a solution of the chloro-enone of Example 12 in 20 ml toluene. The reaction mixture is then stirred at −46° for 22 hours, then at −40° C. for 18 hours, then allowed to warm to 0° over a period of 2 hours. At this time, a TLC (eluant: 50% ethyl acetate/cyclohexane) indicates that the starting chloro-enone ($R_f$=0.54) has been completely consumed. The reaction mixture is then poured into 800 ml hydrochloric acid, extracted with ethyl acetate (2×800 ml), dried over magnesium sulfate, and concentrated in vacuo to leave a red oil, consisting of one major component ($R_f$=0.27) and one minor component ($R_f$=0.40) by TLC. This oil is then chromatographed on 560 g silica gel (gradient elution, 10% to 50% ethyl acetate/cyclohexane). The fractions containing the component of $R_f$=0.40 are pooled and concentrated in vacuo to leave an oil identified as 15-epi-chlorometeneprost by $^1$H-NMR. The fractions containing the component of $R_f$=0.27 are pooled and concentrated in vacuo to leave an oil identified as chlorometeneprost A-14 by $^1$H-NMR.

EXAMPLE 14

Conversion of Chloro-meteneprost into Meteneprost

Refer to Chart A, step 14.

A solution of chloro-meteneprost (138.7 mg, 0.3764 mmoles) in 4 ml dimethylsulfoxide (DMSO) is treated with a solution of potassium cyanide (357.1 mg, 5.494 mmoles) in 4 ml water, then stirred at 100° C. until TLC (eluant: 60% ethyl acetate/cyclohexane) indicates that conversion of chlorometeneprost (Rf=0.53) into a slightly more polar component (Rf=0.47) is complete (21 hr). The reaction mixture is then treated with potassium hydroxide pellets (1.0727 g, 16.28 mmoles) and stirred at 100° C. for another 3.5 hrs. The reaction mixture is then diluted with 50 ml ethyl acetate, washed three times with 30 ml aqueous NaH$_2$PO$_4$, dried over magnesium sulfate, and concentrated in vacuo to leave a pale yellow oil (weight: 138.4 mg) consisting of one major component (Rf=0.49) and several very minor ones by TLC (two elutions with 50:50:1 ethyl acetate/heptane/acetic acid). This pale yellow oil is then chromatographed on 17 g acid-washed silica gel (gradient elution, 2:3:5 to 3:2:5 acetone/heptane/methylene chloride, followed by 50% ethyl acetate/methylene chloride; fraction size, 10 ml). Fractions 22–34 are pooled and concentrated in vacuo to leave a colorless oil, identified as meteneprost completely uncontaminated by the 5,6-trans isomer by $^{13}$C-NMR (signal to noise ratio, approximately 70 to 1) of the derived methyl ester (produced by treatment of a cooled [0° C.] ether solution of meteneprost with excess ethereal diazomethane).

EXAMPLE 14A

Conversion of Chloro-meteneprost into Meteneprost

Refer to Chart A, step 14.

A solution of chloro-meteneprost (4.443 g, 12.06 mmoles) in 40 ml DMF is treated with potassium cyanide (1.562 g, 24.04 mmoles), then stirred at 95° until TLC (eluant: 50% ethyl acetate/cyclohexane) indicates that conversion of the chloro-meteneprost ($r_f$=0.50) into the corresponding nitrile ($R_f$=0.42) is complete (10 hours). The reaction mixture is then poured into 200 ml 3% sodium hydroxide, extracted with ether (3×130 ml), dried over magnesium sulfate, and concentrated in vacuo to leave a light yellow oil (weight: 5.000 g). This oil is then dissolved in 50 ml absolute ethanol, treated with 50 ml 40% potassium hydroxide, and the solution stirred at 95° C. until a TLC (eluant: 75/25/1 ethyl acetate/heptane/acetic acid) indicates that conversion of the nitrile ($R_f$=0.31) into meteneprost ($R_f$=0.23) is complete (9 hours). The reaction mixture is then poured into 750 ml 2.0M sodium dihydrogen phosphate, extracted with ethyl acetate (2×500 ml), dried over magnesium sulfate, and concentrated in vacuo to leave a yellow oil. Although this oil appears homogeneous by TLC, to guarantee homogeneity prior to crystallization it is chromatographed on 370 g acid-washed silica gel (gradient elution, 1/1/2 to 4/1/5 acetone/heptane/methylene chloride). All fractions containing meteneprost are pooled and concentrated in vacuo to leave a colorless oil, identified as meteneprost by HPLC. A portion of this oil (3.503 g, 9.267 mmoles) is then dissolved in 63.0 methanol, treated with a solution of potassium carbonate (599 mg, 4.342 mmoles) in 16 ml water, stirred at room temperature for 5 minutes. The solvents are then removed in vacuo to leave a pale yellow oil, which is dissolved in 37 ml TFH and then concentrated in vacuo. This operation is then performed repeatedly until the residue is a brittle glass (5 times). The glass is then dissolved in 9 ml methanol and added dropwise to a vigorously stirred mixture of 366 ml hexane and 78 ml THF, which causes the product to oil out. The mixture is then seeded. Within minutes, the oil begins to crystallize. The resulting slurry is then stirred vigorously for 10 hours, then the white solid filtered off, triturated with hexane (2×25 ml) and dried by a stream of nitrogen. The final product is a free-flowing, white powder, identified as the potassium salt of meteneprost by combustion analysis. By HPLC, the material is 98.0% pure and contains less than 0.2% by the 5,6-trans isomer.

EXAMPLE 15

Alternative step 9: conversion of chloro-alcohol A-9 into uncyclized nitrile C-1.

Refer to Chart C.

A solution of the crude chloro-alcohol of Example 8 (4.9309 g, 13.97 mmoles) and triphenylphosphine (5.8581 g, 22.36 mmoles) in 20 ml toluene is treated with imidazole (2.8530 g, 41.95 mmoles). The resulting pale yellow suspension is then treated dropwise with a solution of iodine (4.9592 g, 19.52 mmoles) in 50 ml toluene. After the addition is complete (20 min), the reaction mixture (a yellow-orange solution with a gummy orange precipitate) is stirred at room temperature for 50 minutes, diluted with 50 ml ethyl acetate, washed with 100 ml 3% sodium hydroxide, dried over magnesium sulfate, and concentrated in vacuo to leave a yellow oil consisting of a mixture of triphenylphosphine (Rf=0.70), triphenylphosphine oxide (Rf=0.03), and one major organic component (Rf=0.51), but no starting chloro-alcohol (Rf=0.21), by TLC (eluant: 20% ethyl acetate/cyclohexane).

This oil is then taken up in 40 ml DMF, treated with sodium cyanide (2.8731 g, 58.63 mmoles), and stirred at room temperature until TLC indicates that conversion of the component of Rf=0.51 into a mixture of one major product (Rf=0.29) and one very minor product (Rf=0.47) is complete (3.5 hrs). The reaction mixture is then diluted with 100 ml ether, washed twice with 100 ml 5% sodium bicarbonate, dried over magnesium sulfate, and concentrated in vacuo to leave a tan semisolid, which is stirred vigorously 3 times with 40 ml of 20% ethyl acetate/cyclohexane and filtered. The filtrate cake is determined to consist of triphenylphosphine oxide admixed with a small amount of triphenylphosphine. The filter is then concentrated in vacuo to leave a golden brown oil, consisting of a mixture of the two organic products, a large amount of triphenylphosphine, and a small amount of tripenylphosphine oxide by TLC. This oil is then chromatographed on 400 g silica gel (gradient elution, 10% to 25% ethyl acetate/cyclohexane; fraction size, 50 ml). The fractions containing the component of Rf=0.29 (37–49) are combined and concentrated in vacuo to leave a pale yellow oil, identified as an approximately 95:5 mixture of the uncyclized nitrile and its 8 epimer by $^1$H-NMR and $^{13}$C-NMR.

EXAMPLE 16

Alternative step 10: conversion of uncyclized nitrile C-1 to cyclized nitrile C-2.

Refer to Chart C.

A slurry of lithium hexamethyldisilazide (4.5214 g, 27.07 mmoles) in 8 ml toluene is cooled to −20° C. and treated with a solution of the uncyclized nitrile of Example 15 (3.1720 g, 8.762 mmoles) in 8 ml toluene. The reaction mixture is then stirred until TLC (eluant: 30% ethyl acetate/cyclohexane) indicates that conversion of the uncyclized nitrile (Rf=0.51) into one major product (Rf=0.38) and one minor product (Rf=0.45) is about 95% complete (2 hrs). The reaction mixture is then poured into 75 ml 3% sodium hydroxide, extracted twice with 75 ml portions of ethyl acetate, dried over magnesium sulfate and concentrated in vacuo to leave a yellow-brown oil.

A repeat of this procedure employing 549.0 mg (1.5166 mmoles) of uncyclized nitrile yields 682.6 mg of crude product which is chromatographed on 100 g silica gel (gradient elution, 10% to 40% ethyl acetate/cyclohexane; fraction size, 25 ml). The fractions containing the component of Rf=0.45 (23–25) are then combined and concentrated in vacuo to leave a colorless oil, identified as one 9-epimer of the cyclized nitrile by 200 MHz $^1$H-NMR and $^{13}$-C-NMR. The fractions containing the component of Rf=0.38 (27–30) are then combined and concentrated in vacuo to leave a colorless oil, identified as the other 9-epimer of the cyclized nitrile by 200 MHz $^1$H-NMR and $^{13}$C-NMR.

EXAMPLE 17

Alternative step 11: conversion of cyclized nitriles C-2 into 9-methylene-cyclopentane A-12

Refer to Chart C.

A solution of diisopropylamine (3.2 ml; 2.310 g, 22.87 mmoles) in 10 ml THF is cooled to 0° C. treated with n-butyllithium/hexane (10.6 ml of 1.55M solution, 16.43 mmoles), stirred for 10 minutes, cooled to −78° C., and treated with a solution of 2.9570 g of the yellow-brown oil produced in Example 15 (containing 5.573 mmoles of the cyclized nitrile epimers) in 12 ml THF (added dropwise over a period of 4 minutes). The reaction mixture is stirred at −78° C. for 6 minutes, and treated with a solution of iodomethyltributyltin (4.1464 g, 9.627 mmoles) in 10 ml THF. After 15 minutes, the reaction mixture is poured into 200 ml 3% sodium hydroxide, extracted twice with 200 ml of ethyl acetate, dried over magnesium sulfate, and concentrated in vacuo to leave 6.0346 g of a yellow-brown oil, consisting of a mixture of iodomethyltributyltin (Rf=0.77), stannylated nitrile (Rf=0.62), and trace amounts of several other products by TLC (eluant: 30% ethyl acetate/cyclohexane). No starting material (Rf=0.38) is detected.

This yellow-brown oil is then taken up in 18 ml THF, cooled to −78° C. and treated with $CH_3Li.LiBr$/ether (12.5 ml) of 1.4M solution, 17.5 mmoles). After 5 minutes, a TLC plate is spotted with the reaction mixture, eluted with 20% ethyl acetate/cyclohexane, and charred with sulfuric acid. This TLC reveals that conversion of the stannylated nitrile (Rf=0.56) into a slightly more polar product (Rf=0.52) is complete. When this information becomes known (13 minutes after the addition of the iodomethyltributyltin is complete), the reaction mixture is treated with 20 ml methanol to quench the excess $CH_3Li$, poured into 200 ml 3% sodium hydroxide, extracted twice with 200 ml ethyl acetate, dried over magnesium sulfate, and concentrated in vacuo to leaave an orange oil consisting of a mixture of one major organic commponent (Rf=0.52) and tin-containing by-products (Rf=0.82) by TLC. This orange oil is then chromatographed on 400 g silica gel (gradient elution, 10% to 30% ethyl acetate/cyclohexane; fraction size, 50 ml). The fractions containing the component of Rf=0.52 (nos. 22–31) are combined and concentrated in vacuo to leave a pale yellow oil identified as 9-methylene-cyclopentane by $^{13}C$-NMR and $^1H$-NMR.

EXAMPLE 18

Alternate step 10: conversion of cyclized sulfone A-11 to 9-methylene cyclopentane A-12

Refer to Chart A.

A solution of cyclized sulfone A-11 (0.4168 g, 0.9171 mmoles) in 4.0 ml THF is cooled to −78° C. and treated with n-butyllithium/hexane (2.0 ml of 1.6M solution, 3.20 mmoles). The resulting yellow reaction mixture is then treated all at once with neat diiodomethane (0.22 ml, 2.73 mmoles). The resulting light brown reaction mixture is then allowed to warm up to 0° C. and stirred at that temperature for 10 minutes. The reaction mixture is then poured into 100 ml 3% sodium hydroxide, extracted with one 100 ml portion of methylene chloride dried (magnesium sulfate), and concentrated in vacuo to leave a yellow oil, identified as 9-methylene-cyclopentane A-12 in essentially pure form by TLC (eluant: 20% ethyl acetate/cyclohexane) and $^1H$-NMR.

EXAMPLE 19

Alternative step 11: conversion of cyclized sulfone A-11 into 9-methylene cyclopentane A-12

Refer to Chart A, step 11.

A solution of cyclized sulfone A-11 (10.006 g, 22.01 mmoles) in 60 ml THF is cooled to −78° C., then treated over a period of 1 minute with n-butyllithium/hexane (18.0 ml of 1.6M solution, 28.8 mmoles), which causes the internal temperature to rise to −40° C. The reaction mixture is then re-cooled to −65° C. and treated all at once with neat 2-ethoxymethoxy-methyl chloride (4.0 ml, 4.364 g, 35.05 mmoles), which causes the internal temperature to rise to −40° C. A TLC (eluant: 40% ethyl acetate/cyclohexane) taken immediately after this addition indicates that conversion of the starting material (Rf=0.46) into the product (Rf=0.37) is complete. The reaction mixture is then diluted with 125 ml methanol and treated in succession with solid sodium dihydrogen phosphate (12.496 g, 88.00 mmoles) and 5.98% sodium amalgam (67.69 g, 176.0 mmoles). The resulting gray slurry is then warmed to 0° C. and stirred at that temperature until a TLC indicates that conversion of the Rf=0.37 component into a less polar component (Rf=0.70) is complete (3.5 hours). The reaction mixture is then poured into 1 l 3% NaOH and extracted with ethyl acetate (2×750 ml). The extracts are then combined, dried over magnesium sulfate, and concentrated in vacuo to leave a pale yellow oil, identified as 9-methylene-cyclopentane A-12 in essentially pure form by TLC and $^1H$-NMR.

EXAMPLE 20

Alternative step 11: conversion of cyclized sulfone A-11 into 9-methylene cyclopentane A-12

Refer to Chart A, step 11.

A solution of the cyclized sulfone of Example 10 (10.006 g, 22.02 mmoles) in 90 ml THF is cooled to −74° C., then treated with nBuLi/hexane (15.1 ml of 1.6M solution, 24.2 mmoles), which causes the temperature to rise to −55° C. The resulting orange reaction mixture is then re-cooled to −74° C., treated with diisopropylamine (0.70 ml, 5.00 mmoles), warmed to −37° C., then treated with a solution of iodomethyltributyltim (13.827 g, 32.11 mmoles) in 10 ml of THF, which causes the temperature to rise to −25° C. The reaction mixture is then stirred at −20° C. until TLC analysis (eluant: 30% ethyl acetate/cyclohexane) indicates that conversion of the starting material (Rf=0.21) into a less polar component (Rf=0.48) is complete (50 minutes). The reaction mixture is then cooled to −74° C., and treated with n-butyllithium/hexane dropwise until a TLC indicates that conversion of the Rf=0.48 component into the 9-methylene-cyclopentane (Rf=0.54) is complete (26.2 ml of 1.6M solution, 41.9 mmoles). During this addition, the temperature rises to −44° C. When the addition is complete, the reaction mixture is quenched with 2 ml methanol, poured into 750 ml 3% sodium hydroxide, and shaken with 750 ml methylene chloride, which results in formation of an emulsion. This emulsion is then broken by filtration through celite. The methylene chloride layer is then separated and the aqueous layer extracted with ethyl acetate (2×500 ml). The organic extracts are then combined, washed with 500 ml saturated sodium chloride, dried vover magnesium sulfate, and concentrated in vacuo to leave an orange oil, identified as a mixture of the 9-methylene cyclopentane A-12 and tin-containing by-products (Rf=0.65) by TLC and $^1H$-NMR.

FORMULAS
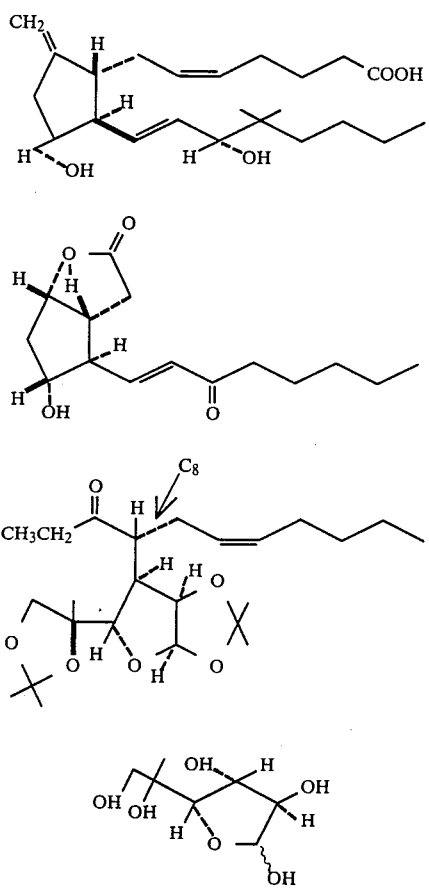
I
II
III
D-Glucose
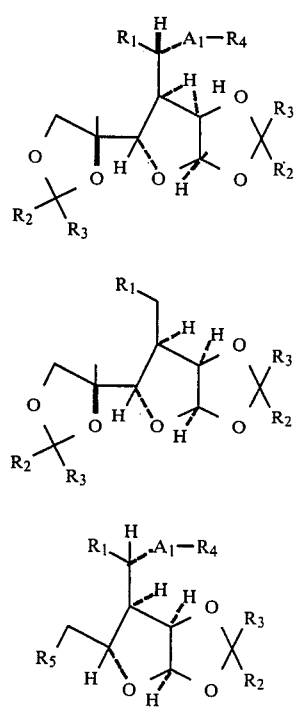
A-6A
A-5A
A-7A
-continued
FORMULAS
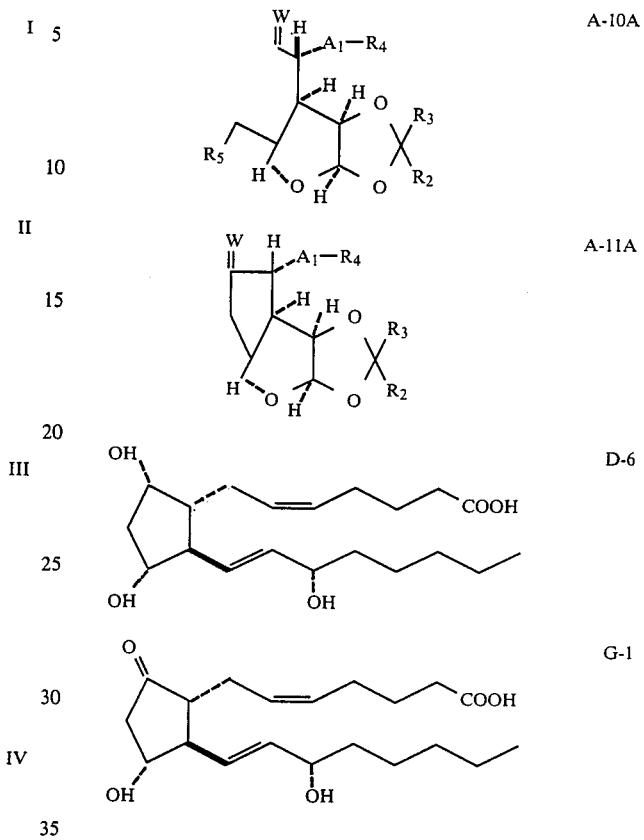
A-10A
A-11A
D-6
G-1
CHART A
Step 1 (Isopropylidenation):
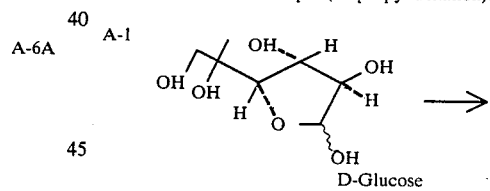
A-1
D-Glucose
Step 2 (Oxidation):
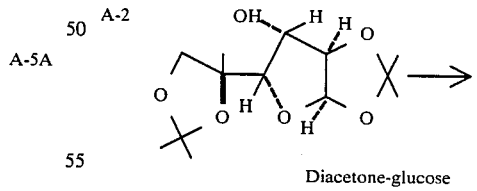
A-2
Diacetone-glucose
Step 3 (Emmons Condensation):
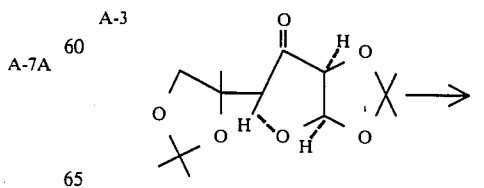
A-3
Diacetone-glucose-Ketone
Step 4 (Hydrogenation):

-continued
CHART A

A-4 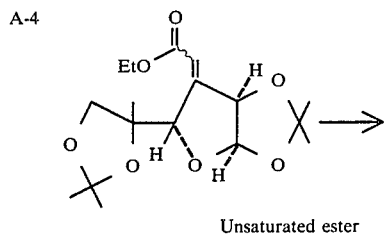
Unsaturated ester

Step 5 (Stereoselective Alkylation):

A-5 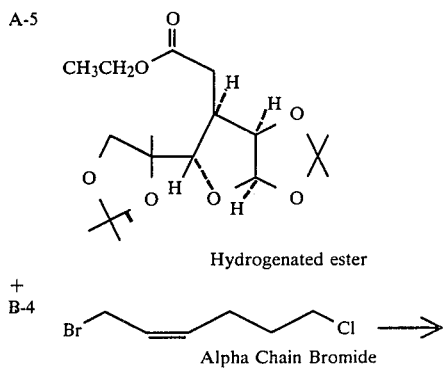
Hydrogenated ester

+
B-4 Br—CH=CH—Cl
Alpha Chain Bromide

Step 6 (Cleavage of Acetonide):

A-6 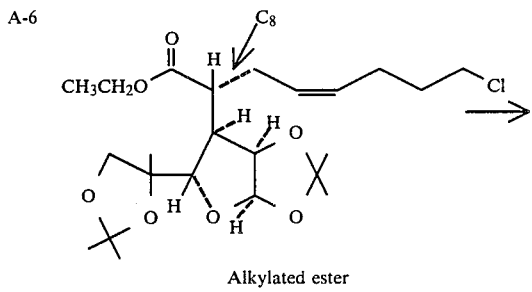
Alkylated ester

Step 7 (Chlorination):

A-7 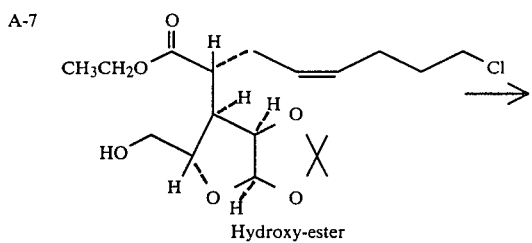
Hydroxy-ester

Step 8 (Reduction):

A-8 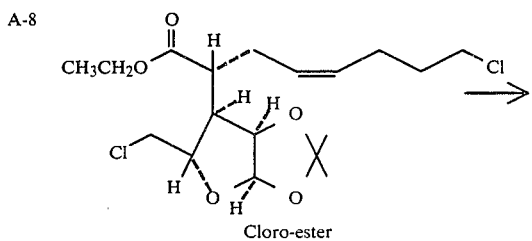
Cloro-ester

Step 9 (Sulfonation):

-continued
CHART A

A-9 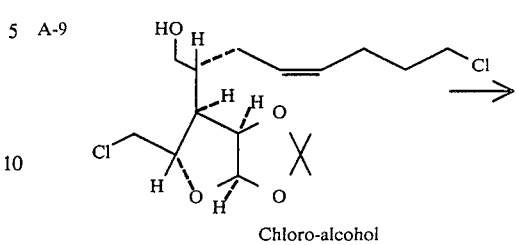
Chloro-alcohol

Step 10 (Cyclization):

A-10 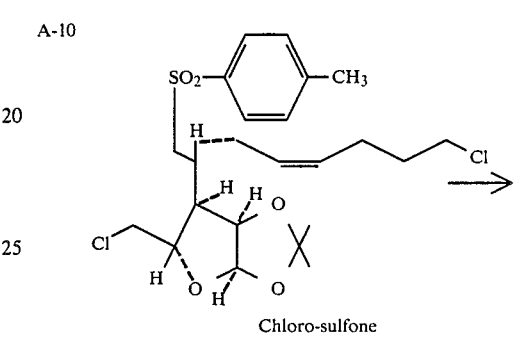
Chloro-sulfone

Step 11 (Methylenation):

A-11 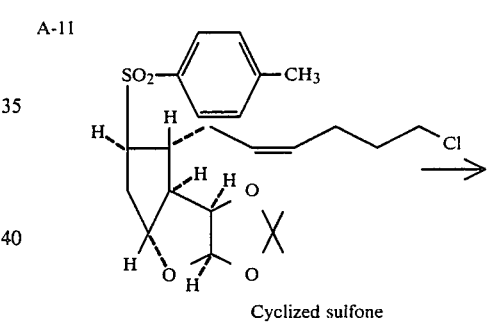
Cyclized sulfone

Step 12 (Attachment of Beta Chain):

A-12 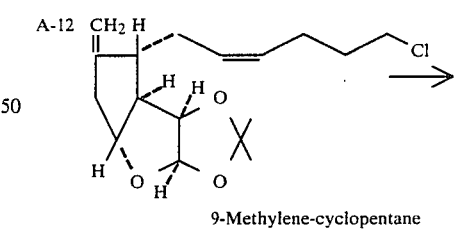
9-Methylene-cyclopentane

Step 13 (DIABAL/BHT Reduction):

A-13 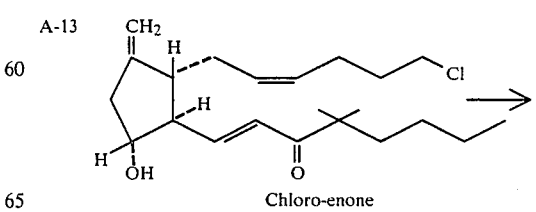
Chloro-enone

Step 14 (Displacement of Chloride):

-continued
CHART A

A-14 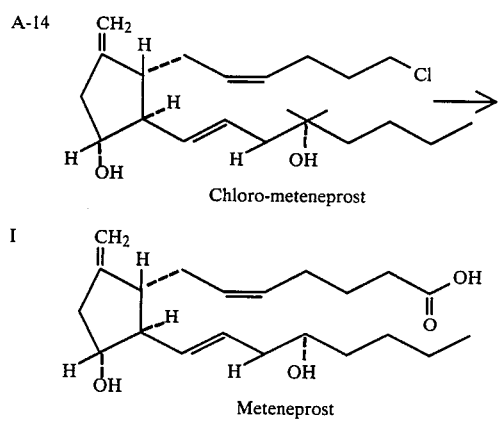
Chloro-meteneprost

I
Meteneprost

CHART B

Step 1 (Alkylation of Propargyl Alcohol):

B-1 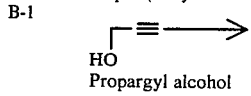
Propargyl alcohol

Step 2 (Semi-Hydrogenation):

B-2 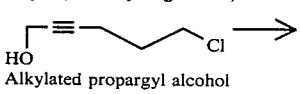
Alkylated propargyl alcohol

Step 3 (Bromination):

B-3 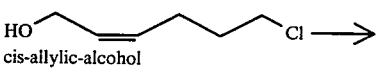
cis-allylic-alcohol

B-4 
Alpha-chain-bromide

CHART C

A-9 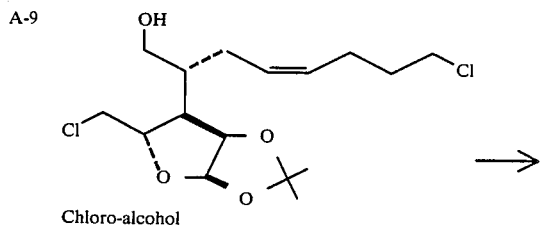
Chloro-alcohol

C-1 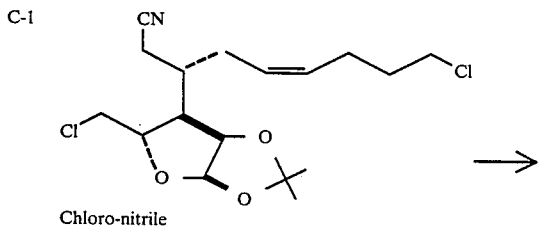
Chloro-nitrile

C-2 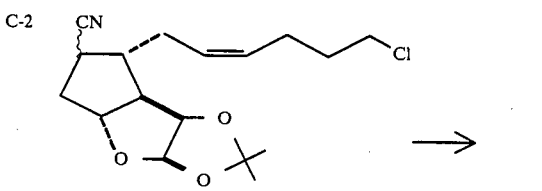

-continued
CHART C

5  Cyclized nitrile

A-12 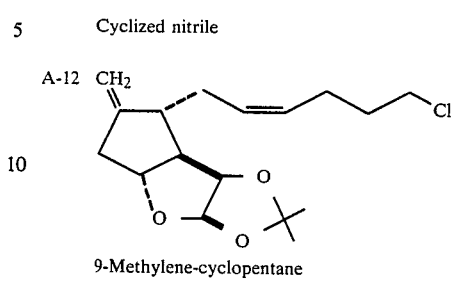

9-Methylene-cyclopentane

CHART D

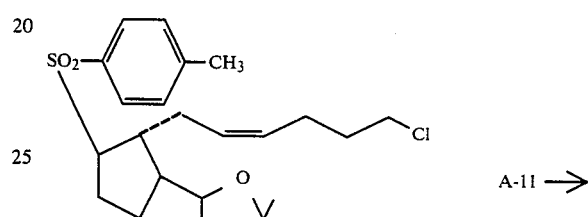 A-11 →

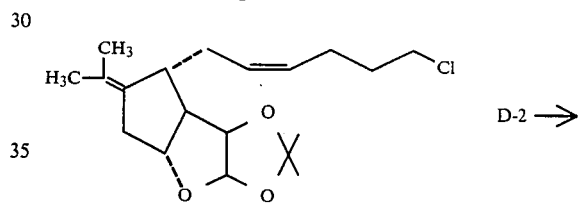 D-2 →

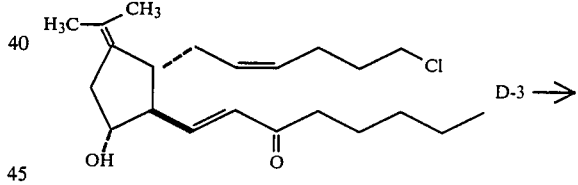 D-3 →

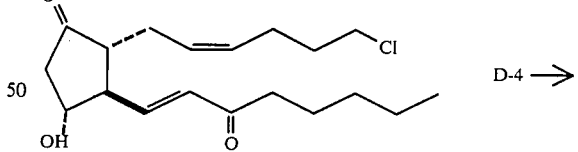 D-4 →

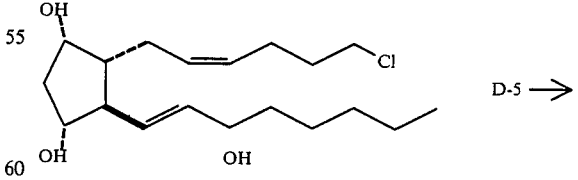 D-5 →

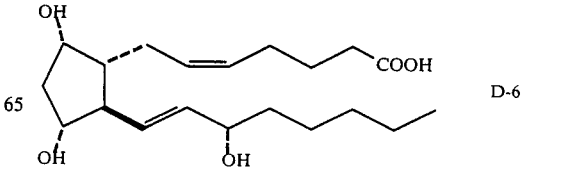 D-6

CHART E
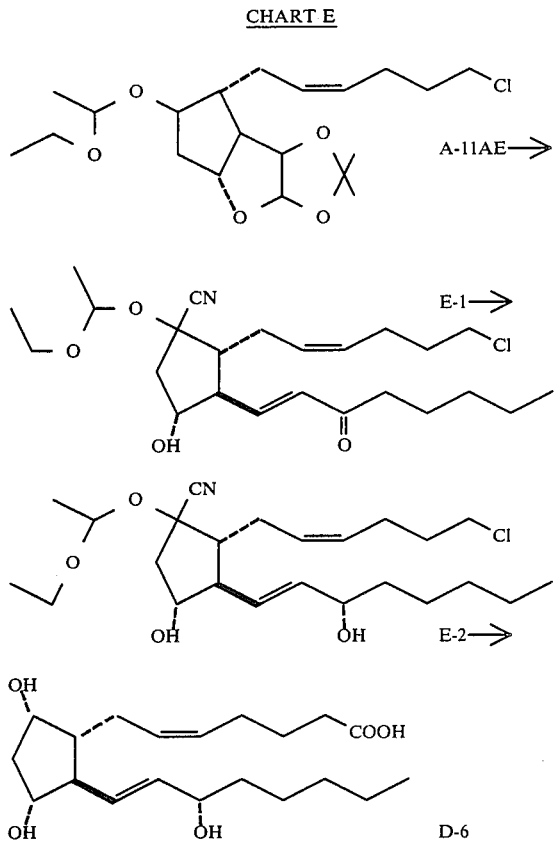
CHART F
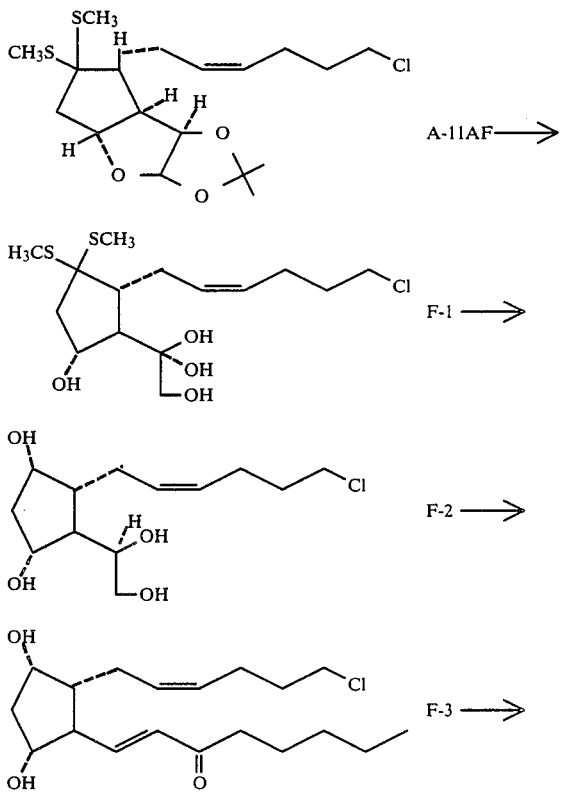
CHART F (continued)
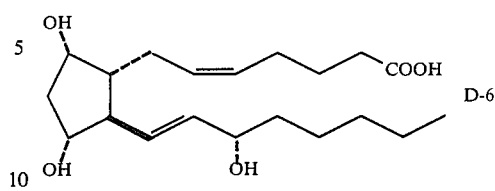
CHART G
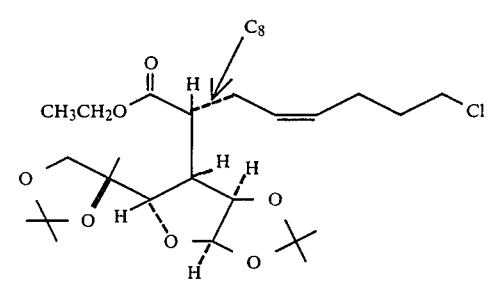
I claim:
1. A process for preparing a prostaglandin intermediate of the formula A-6
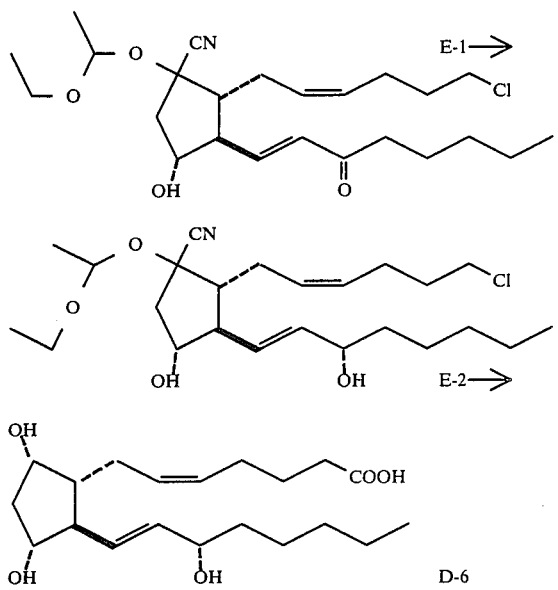
which comprises:
(a) treating a compound of the formula A-5

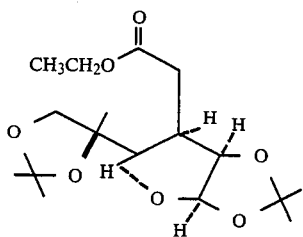
A-5
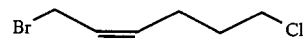
B-4
with a weakly nucleophilic strong base in an inert solvent, and, subsequently
(b) reacting the formula A-5 compound with an alkylating agent of the formula B-4
at a temperature in the range of about −110° to about 0° C.
* * * * *

UNITED STATES PATENT OFFICE
CERTIFICATE OF CORRECTION

Patent No. 4,549,030　　　　　　　　Dated 22 October 1985

Inventor(s)　　B.A. Pearlman

It is certified that error appears in the above-identified patent and that said Letters Patent are hereby corrected as shown below:

Column 3, line 40, "$(C_24C_5)$" should read -- $(C_1-C_5)$ --.

Column 5, line 2, "$-SO(CH_6H_5)$;" should read -- $-SO(C_6H_5)$; --.

Column 20, line 10, "$(120^o-$" should read -- $(128^o-$ --.

Column 21, line 8, "Soc. Comm." should read -- Soc. Chem. Comm. --.

Column 27, line 25, "pclant" should read -- polar --.

Column 29, line 49, "by" should read -- of --.

Column 33, Formula I, that portion of the formula should read as follows:

Column 33, Formula II, that portion of the formula should read as follows:

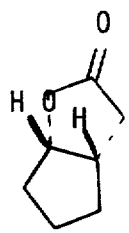

UNITED STATES PATENT OFFICE
CERTIFICATE OF CORRECTION

Patent No. 4,549,030  Dated 22 October 1985

Inventor(s) B.A. Pearlman

It is certified that error appears in the above-identified patent and that said Letters Patent are hereby corrected as shown below:

Column 33, Formula A-6A, that portion of the formula should read as follows:

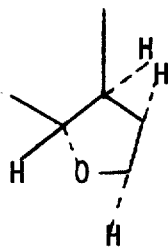

Column 34, Formula A-10A, that portion of the formula should read as follows:

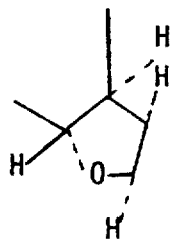

Column 34, Formula A-11A, that portion of the formula should read as follows:

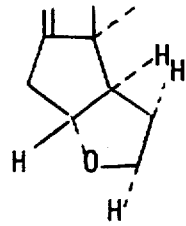

UNITED STATES PATENT OFFICE
CERTIFICATE OF CORRECTION

Patent No. 4,549,030  Dated 22 October 1985

Inventor(s) B.A. Pearlman

It is certified that error appears in the above-identified patent and that said Letters Patent are hereby corrected as shown below:

Column 34, Formula A-3, that portion of the formula should read as follows:

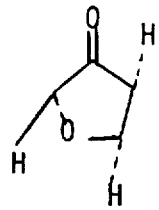

Column 35, Formula A-5, that portion of the formula should read as follows:

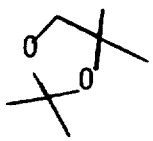

Column 36, Formula A-10, that portion of the formula should read as follows:

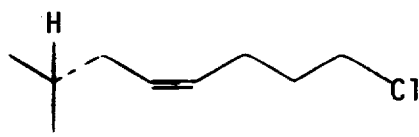

UNITED STATES PATENT OFFICE
CERTIFICATE OF CORRECTION

Patent No. 4,549,030   Dated 22 October 1985

Inventor(s)  B.A. Pearlman

It is certified that error appears in the above-identified patent and that said Letters Patent are hereby corrected as shown below:

Column 37, Formula A-14, that portion of the formula should read as follows:

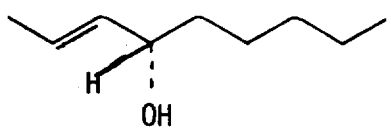

Column 37, Formula I, that portion of the formula should read as follows:

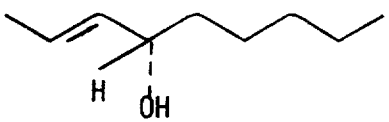

Column 38, Formula D-5, that portion of the formula should read as follows:

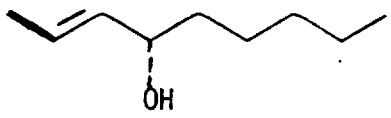

Column 39, Formula A-11AF, that portion of the formula should read as follows

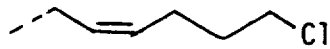

UNITED STATES PATENT OFFICE
CERTIFICATE OF CORRECTION

Patent No. 4,549,030      Dated 22 October 1985

Inventor(s) B.A. Pearlman

It is certified that error appears in the above-identified patent and that said Letters Patent are hereby corrected as shown below:

Column 41, Formula A-5, that portion of the formula should read as follows:

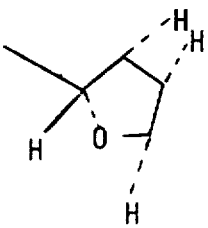

Signed and Sealed this

Fourteenth Day of October, 1986

[SEAL]

*Attest:*

DONALD J. QUIGG

*Attesting Officer*     *Commissioner of Patents and Trademarks*